(12) United States Patent
Choi et al.

(10) Patent No.: US 8,524,243 B2
(45) Date of Patent: Sep. 3, 2013

(54) **AVIRULENT *SALMONELLA GALLINARUM* VARIANTS AND PHARMACEUTICAL COMPOSITION USING THE SAME**

(75) Inventors: Hyang Choi, Anyang-si (KR); Soo An Shin, Seoul (KR); Si Yong Yang, Incheon (KR); Young Wook Cho, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/618,169

(22) Filed: Sep. 14, 2012

(65) Prior Publication Data

US 2013/0022574 A1    Jan. 24, 2013

Related U.S. Application Data

(62) Division of application No. 13/274,854, filed on Oct. 17, 2011.

(60) Provisional application No. 61/487,137, filed on May 17, 2011.

(51) Int. Cl.
*A61K 39/112* (2006.01)
*C12N 1/20* (2006.01)

(52) U.S. Cl.
USPC .................. 424/184.1; 424/258.1; 424/235.1; 435/252.3

(58) Field of Classification Search
None
See application file for complete search history.

(56) References Cited

U.S. PATENT DOCUMENTS

| | | | |
|---|---|---|---|
| 6,923,957 B2 | 8/2005 | Lowery et al. | |
| 7,211,264 B2 | 5/2007 | Feldman et al. | |
| 7,700,104 B2 * | 4/2010 | Hensel et al. | 424/184.1 |
| 7,842,290 B2 * | 11/2010 | Holden | 424/93.2 |
| 7,887,816 B2 * | 2/2011 | Feldman et al. | 424/258.1 |
| 7,955,600 B2 * | 6/2011 | Hensel et al. | 424/184.1 |
| 2012/0294892 A1 | 11/2012 | Choi et al. | |

OTHER PUBLICATIONS

Abrahams, G.L. and Hensel, M., "Manipulating cellular transport and immune responses: dynamic interactions between intracellular *Salmonella enterica* and its host cells," *Cell. Microbiol.* 8(5): 728-37, Blackwell Publishing Ltd., United Kingdom (2006).

Brumme, S., et al., "Impact of *Salmonella typhimurium* DT104 virulence factors *invC* and *sseD* on the onset, clinical course, colonization patterns and immune response of porcine salmonellosis," *Vet. Microbiol.* 124:274-85, Elsevier B.V., Netherlands (2007).

Desin, T.S., et al., "*Salmonella enterica* Serovar Enteritidis Pathogenicity Island 1 Is Not Essential for but Facilitates Rapid Systematic Spread in Chickens," *Infect. Immun.* 77(7):2866-75, American Society for Microbiology, United States (2009).

Edwards, R.A., et al., "A role for *Salmonella* fimbriae in intraperitoneal infections," *Proc. Natl. Acad. Sci.* 97:1258-1262, National Academy of Sciences, United States (2000).

Edwards, R.A., et al., "Comparative genomics of closely related salmonellae," *Trends Microbiol.* 10(2):94-99, Elsevier Science Ltd., United Kingdom (2001).

Gulig, P.A., et al., "Molecular analysis of *spv* virulence genes of the *Salmonella* virulence plasmids," *Mol. Microbiol.* 7(6);825-30, Blackwell Scientific, United Kingdom (1993).

Hapfelmeier, S., et al., "The *Salmonella* Pathogenicity Island (SPI)-2 and SPI-1 Type III Secretion Systems Allow *Salmonella* Serovar *typhimurium* to Trigger Colitis via MyD88-Dependent and MyD88-Independent Mechanisms," *J. Immunol.* 174:1675-85, The American Associaton of Immunologists, Inc., United States (2005).

Kimbrough, T.G. and Miller, S.I., "Assembly of the type III secretion needle complex of *Salmonella typhimurium*," *Microbes Infect.* 4:75-82, Elsevier SAS, France (2002).

Lostroh, C.P. and Lee, C.A., "The *Salmonella* pathogenicity island-1 type III secretion system," *Microbes Infect.* 3:1281-91, Elsevier SAS, France (2001).

Schlumberger, M.C. and Hardt, W-D., "*Salmonella* type III secretion effectors: pulling the host cell's strings," *Curr. Opin. Microbiol.* 9:46-54, Current Biology, United Kingdom (2006).

Waterman, S.R. and Holden, D.W., "Function and effectors of the *Salmonella* pathogenicity island 2 type III secretion system," *Cell. Microbiol.* 5(8):501-11, Blackwell Publishing Ltd., United Kingdom (2003).

Office Action dated Oct. 17, 2012, in U.S. Appl. No. 13/274,854, Choi, H., et al., filed Oct. 17, 2011.

\* cited by examiner

*Primary Examiner* — Padma V Baskar
(74) *Attorney, Agent, or Firm* — Sterne, Kessler, Goldstein & Fox P.L.L.C.

(57) ABSTRACT

The present invention relates to avirulent *Salmonella Gallinarum* variants by inactivating virulence gene clusters of *Salmonella Gallinarum* (SG), a main pathogen of avian salmonellosis, and various uses thereof notably in the production of *Salmonella*-specific lytic bacteriophages, pharmaceutical compositions and feed additives.

6 Claims, 2 Drawing Sheets

AVIRULENT *SALMONELLA GALLINARUM* VARIANTS AND PHARMACEUTICAL COMPOSITION USING THE SAME

REFERENCE TO A SEQUENCE LISTING SUBMITTED ELECTRONICALLY VIA EFS-WEB

This application is a divisional application of U.S. application Ser. No. 13/274,854, filed Oct. 17, 2011, which claims the benefit of the filing date of U.S. application Ser. No. 61/487,137, filed May 17, 2011.

The content of the electronically submitted sequence listing, file name: 2511_0120002_SEQ_ID_Listing.ascii.txt; size: 95,695 bytes; and date of creation: Sep. 14, 2012, filed herewith, is incorporated herein by reference in its entirety.

BACKGROUND OF THE INVENTION

1. Field of the Invention

The present invention provides avirulent *Salmonella* variants and various uses thereof, particularly in the production of *Salmonella*-specific lytic bacteriophages, pharmaceutical compositions, and feed additives.

2. Description of the Related Art

Currently over 2,000 *Salmonella* strains are generally classified into host-specific serotypes, and non-host-specific serotypes pathogenic for both animals and humans. Representative among fowl-adapted pathogens are *Salmonella Gallinarum* (SG) and *Salmonella Pullorum* (SP) which are known to cause fowl typhoid and *pullorum* disease, respectively. These *Salmonella*-caused fowl diseases occur at low frequency in advanced countries, but have inflicted tremendous economic damage on the poultry farming in developing countries.

*Salmonella Gallinarum* strains have serologically the same somatic antigen (O-antigen) structures and are classified as being non-motile because they have no flagella. When entering into a host animal via contaminated feed or a contaminated environment, *Salmonella* pass through the gastrointestinal tract, and invade intestinal epithelial cells by interaction with Peyer's patch M (microfold) cells and penetrate into the intestinal membrane. *Salmonella* are transported by the M cells to macrophages in adjacent intestinal membranes, and then *Salmonella* infection develops into a systemic disease.

The type III secretion system (TTSS) is a protein appendage found in Gram-negative bacteria, which consists of a needle-like protein complex structure through which virulence effector proteins pass from the bacterial cytoplasm directly into the host cytoplasm (Mota L J et al., Ann Med. (2005);37(4):234-249). The type III secretion system is essential for the delivery of the pathogenicity of *Salmonella* (Schlumberger M C et al., Curr Opin Microbiol. (2006);9(1): 46-54). Wild-type *Salmonella* take advantage of TTSS when adhering to and invading host cells, and then survives during the phagocytosis of macrophages and circulates throughout the body via the bloodstream, causing a systemic infection. Hence, *Salmonella* infection cannot proceed without the normal operation of TTSS. *Salmonella* pathogenicity island-1 (hereinafter referred to as "SPI-1") is a discrete region of the *Salmonella* chromosome encoding the type III secretion system and virulent effector proteins which are necessary for invasion into intestinal epithelial cells in the early stage of infection (Kimbrough T G et al., Microbes Infect, (2002);4 (1):75-82). *Salmonella* pathogenicity island-2 (hereinafter referred to as "SPI-2") is also a discrete region of the *Salmonella* chromosome encoding the type III secretion system and effector proteins which involved in survival and proliferation during phagocytosis by macrophages in intestinal immune organs or immune organs such as the spleen and the liver after translocation across epithelial cells (Waterman S R et al., Cell Microbiol, (2003);5(8):501~511, Abrahams G L, Cell Microbiol, (2006);8(5):728-737). Genes within SPI-1 and SPI-2 and their functions are summarized in Table 1, below.

TABLE 1

| Gene | | Characteristics |
|---|---|---|
| SPI-1 | avrA | putative inner membrane protein |
| | sprB | transcriptional regulator |
| | hilC | bacterial regulatory helix-turn-helix proteins, araC family |
| | orgA | putative flagellar biosynthesis/type III secretory pathway protein |
| | prgK | cell invasion protein; lipoprotein, may link inner and outer membranes |
| | prgJIH | cell invasion protein |
| | hilD | regulatory helix-turn-helix proteins, araC family |
| | hilA | invasion genes transcription activator |
| | iagB | cell invasion protein |
| | sptP | protein tyrosine phosphate |
| | sicP | chaperone, related to virulence |
| | iacP | putative acyl carrier protein |
| | sipADCB | cell invasion protein |
| | sicA | surface presentation of antigens; secretory proteins |
| | spaSRQPO | surface presentation of antigens; secretory proteins |
| | invJICB | surface presentation of antigens; secretory proteins |
| | invAEGFH | invasion protein |
| SPI-2 | ssaUTSRQPON VMLKJIHG | Secretion system apparatus |
| | sseGF | Secretion system effector |
| | sscB | Secretion system chaperone |
| | sseEDC | Secretion system effector |
| | sscA | Secretion system chaperone |
| | sseBA | Secretion system effector |
| | ssaE | Secretion system effector |
| | ssaDCB | Secretion system apparatus |
| | ssrA | Secretion system regulator: Sensor component |
| | ssrB | Secretion system regulator: transcriptional activator, homologous with degU/uvrY/bvgA |

In addition to these type III secretion systems, fimbriae gene (faeHI) (Edwards R A et al., PNAS (2000); 97 (3):1258-1262) and the virulent factor (spvRABCD operon) present in virulent plasmids of *Salmonella* are implicated in the virulence of *Salmonella* (Gulig P A et al., Mol Microbiol (1993); 7(6):825-830).

*Salmonella*-caused fowl diseases are difficult to control because they are transmitted in various ways including egg transmission, and feed or environmental infection, and show high recurrence rates even after post-infectious treatment with antibiotics. Therefore, it is importance of preventing the onset of disease by using a vaccine as well as sanitizing breeding farms and feed. In the poultry industry, a lot of effort has been poured into the use of live vaccines (attenuated *Salmonella Gallinarum* strains—SG9S, SG9R) and dead vaccines (gel vaccines, oil vaccines, etc.) to prevent the onset of fowl typhoid. However, the effects of the vaccine vary with the concentration of the vaccine used, the condition of the fowl vaccinated, and the environment of chicken houses. And, the efficacy of these vaccines is reported to be significantly lower than that of the vaccines for other diseases. Treatment with antibiotics, although reducing the lesion, converts infected fowls into chronic carriers (See: Incidence and Prevention of Hen Salmonellosis, the National Veterinary Research & Quarantine Service, Korea).

Therefore, new *Salmonella*-controlling approaches that are better than conventional vaccines or antibiotics are being demanded. Many scientists have recently paid attention to bacteriophages, which infect and lyse bacteria specifically and are safe to humans, as a potent alternative to antibiotics. There are many reports concerning the use of bacteriophages being used in the prevention or therapy of *Salmonella* diseases (Atterbury R J et al., Appl Environ Microbiol, (2007); 73 (14):4543-4549) and as disinfectants or detergents to prevent the putrefaction of foods (PCT 1998-08944, PCT 1995-31562, EP 1990-202169, PCT 1990-03122), and concerning phage display techniques for diagnosis (Ripp S et al., J Appl Microbiol, (2006);100(3):488-499), *Salmonella* vaccines prepared by deleting or modifying one or two genes within SPI-2 gene cluster have recently been disclosed (U.S. Pat. Nos. 6,923,957, 7,211,264, and 7,887,816).

For industrial use, bacteriophages are produced by separating the phage progenies from the host cells lysed during the proliferation of bacteriophages which have been inoculated into the host cells cultured on a mass scale. As for bacteriophages specific for pathogenic bacteria, however, their lysates may contain the pathogenic host cells being not removed, and/or virulent materials such as pathogenic proteins of the host. This likelihood acts as a great risk factor to the safety of bacteriophages produced on the basis of pathogenic host cells.

Many bacteria have lysogenic phages on their chromosomes; however, most of the phages are cryptic and cannot produce progeny because of the accumulation of many mutations as ancestral remnants. Lysogenic phages, although inactive, may help the survival capacity of *Salmonella* upon host infection because they contain the genes necessary for lytic and lysogenic growth and some of the genes encode pathogenic factors. However, these genes are likely to undergo homologous recombination with the viral genome of other similar phages which newly infect animals, thus producing genetically modified phages. As for the typical *Salmonella typhimurium*, it has fels-1, fels-2, gifsy-1, and gifsy-2 prophages and two cryptic phages. In contrast, *Salmonella Gallinarum* could be used as a phage-producing host since *Salmonella Gallinarum* have neither prophages nor cryptic phages, and then are not genetically modified by recombination, (Edwards P A et al, Trends Microbiol, (2002); 10(2):94-99).

For the purpose of minimizing toxic remnants during progeny production and phage's opportunity for mutation, the present inventors designed the idea that the virulence gene clusters of *Salmonella Gallinarum* could be inactivated for producing bacteriophages. There have no precedent cases wherein avirulent bacteria, which had been converted from virulent bacteria by inactivating a virulence gene cluster, were used as a bacteriophage host cell.

In addition to the production of bacteriophages, the *Salmonella* deprived of virulence by inactivating virulence gene clusters are themselves used for developing attenuated live vaccines for controlling *Salmonella* or applied to the bioindustry, guaranteeing significant added values.

In the present invention, avirulent *Salmonella Gallinarum* variants obtained by inactivating at least one of the main *Salmonella* virulence gene clusters (SPI-1, SPI-2, spvRABCD and faeHI operons) are used as a bacteriophage-producing host cell and applied to various uses.

SUMMARY OF THE INVENTION

With the aim of solving the problems with the recombinational modification of progeny phages and the toxic bacterial remnants in the course of bacteriophage production on the basis of the above-described facts, the present inventors developed avirulent *Salmonella Gallinarum* variants as a host cell for bacteriophage-producing by inactivating at least one of the four main *Salmonella. Gallinarum* gene clusters (SPI-1, SPI-2, spvRABCD and faeHI operons). In addition, the present inventors primarily confirmed reduced virulence by measuring the efficiency of the invasion of *Salmonella Gallinarum* into avian epithelial cells, and reconfirmed by measuring the mortality of hens infected with avirulent *Salmonella Gallinarum* variants. On the other hand, the present inventors approve the use of bacteriophage-producing host, the use of the pharmaceutical compositions and feed additives for the prevention or treatment of avian salmonellosis through comparison of the productivity of bacteriophages between wild-type and the avirulent *Salmonella Gallinarum* variants.

It is therefore a primary object of the present invention to provide a *Salmonella Gallinarum* variant in which the SPI-2 gene cluster is inactivated, a *Salmonella Gallinarum* variant in which both SPI-1 and SPI-2 gene clusters are inactivated, and an avirulent *Salmonella Gallinarum* variant in which at least one of the four main virulence gene clusters (SPI-1, SPI-2, spvRABCD, and faeHI operon) has been inactivated.

It is another object of the present invention to provide the use of the avirulent *Salmonella Gallinarum* variant in the production of *Salmonella*-specific bacteriophages or a method for producing phages using the avirulent *Salmonella Gallinarum* variant. The avirulent *Salmonella Gallinarum* variants according to the present invention can be used for the mass-production of *Salmonella*-specific lytic bacteriophages free of remnant toxicity and applied to the development of a novel concept of antibiotic substitutes which have high industrial utility value and guarantee significant added value.

It is a further object of the present invention to provide a pharmaceutical composition comprising avirulent *Salmonella Gallinarum* variants as an active ingredient, preferably a live vaccine and a feed additive. The SPI-1 gene cluster encodes type III secretion system proteins which remain on cell surfaces, acting as an antigen while the SPI-2 gene cluster encodes proteins which are involved in survival in the phagosomes after passage across epithelial cells. Hence, the inactivation of the SPI-2 gene cluster alone, with SPI-1 gene cluster remaining intact, leaves the antigen necessary for the production of an antibody inducing an immune response, but does not allow the bacteria to survive during phagocytosis, which does not result in a systemic disease. Thus, the SPI-2 gene cluster-inactivated *Salmonella Gallinarum* variant might be used as a live vaccine.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
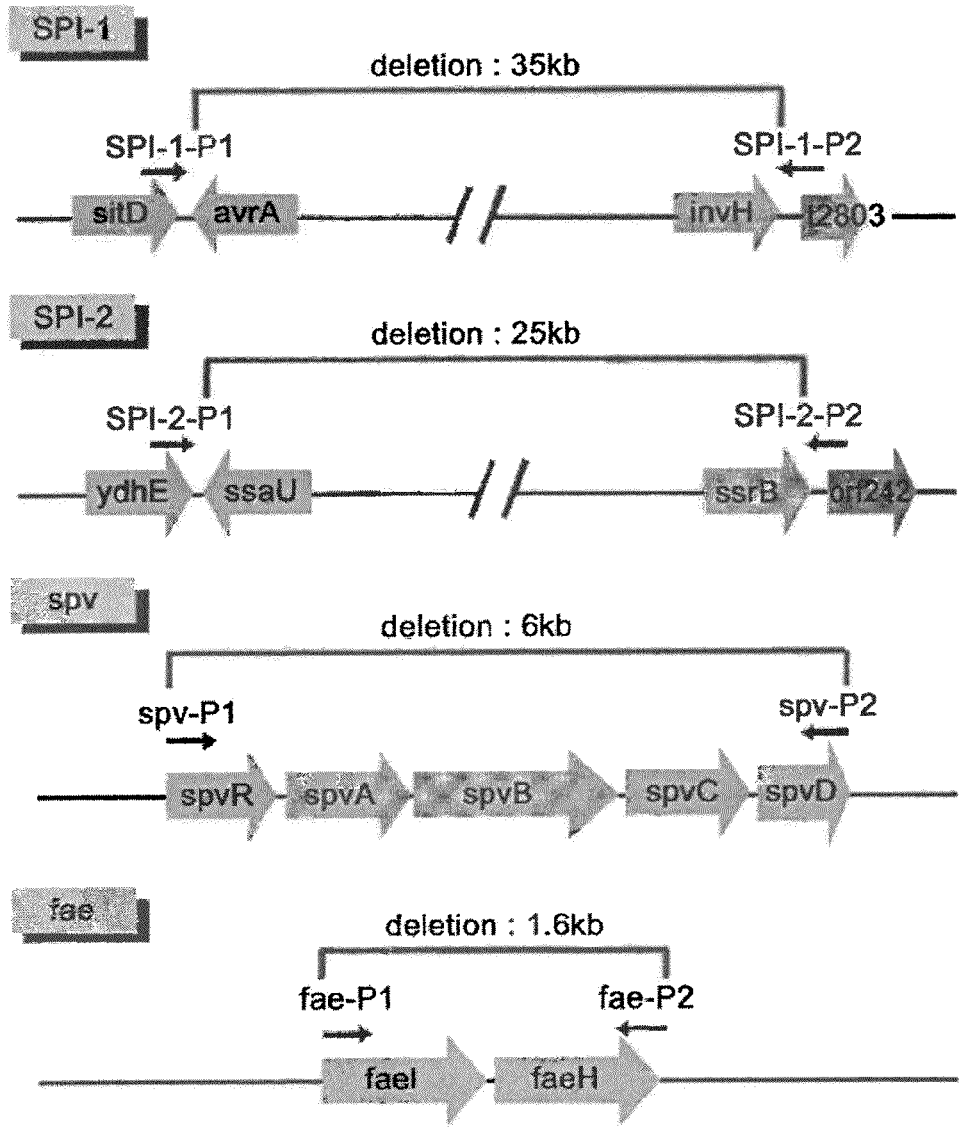
FIG. 1 is a schematic diagram showing virulence genes of avian *Salmonella* (Salmonella pathogenicity island-1, *Salmonella* pathogenicity island-2, spvRABCD, faeHI) and sites corresponding to primers for inactivating the virulence genes.
Figure 2:
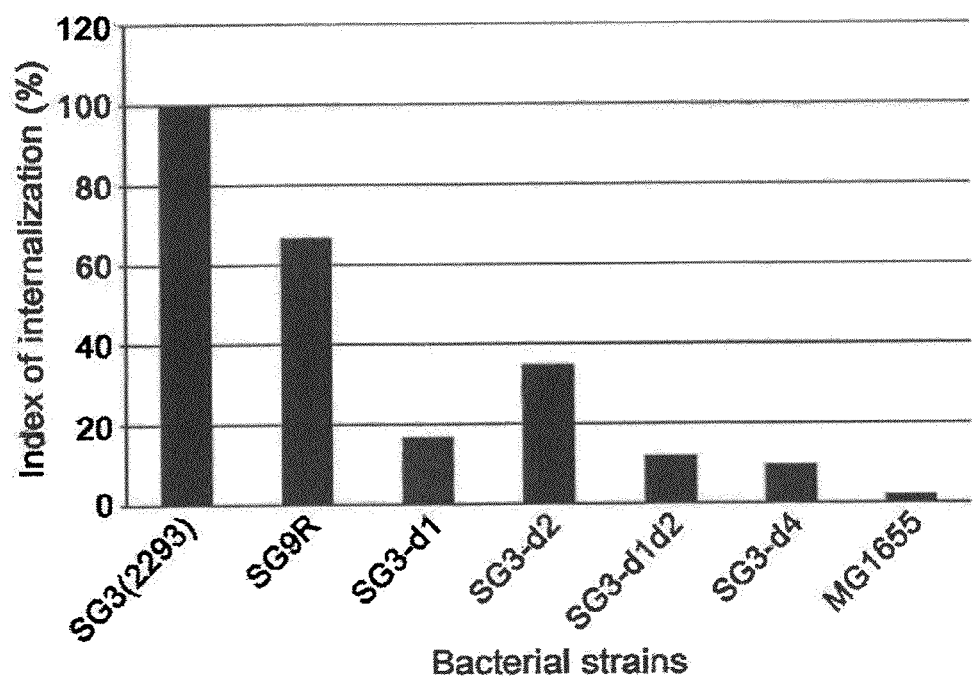
FIG. 2 is a graph showing the efficiency of the in vitro invasion into avian epithelial cells of the virulence gene-inactivated *Salmonella Gallinarum* variants (SG3-d1, SG3-d2, SG3-d1d2, SG3-d4), together with controls wild-type *Salmonella Gallinarum* SG2293), *Salmonella Gallinarum* live vaccine (SG9R), and non-pathogenic *E. coli* (MG1655). Invasion efficiency is expressed as a percentage of the count of microorganisms within cells divided with the count of microorganisms within a culture medium. The microorganisms were used at a concentration of $8.0 \times 10^7$ cfu per well.

In order to accomplish the above objects, an aspect of the present invention provides the avirulent *Salmonella Gallinarum* variants which are remarkably decreased in pathogenicity.

The *Salmonella Gallinarum* variants are rendered avirulent by inactivating at least one of the virulence gene clusters *Salmonella* pathogenicity island-1, *Salmonella* Pathogenicity Island-2, spvRABCDf and faeHI.

As used herein, the term "virulence gene clusters of *Salmonella*" refers to the four gene clusters involved in the virulence of *Salmonella Gallinarum*, including the *Salmonella* Pathogenicity Island-1 (hereinafter referred to as "SPI-1") operon coding for the structural proteins and toxic effector proteins of type III secretion system, the *Salmonella* Pathogenicity Island-2 (hereinafter referred to as "SPI-2") operon coding for the structural proteins and toxic effector proteins of type III secretion system, the spvRABCD operon coding for pathogenically active proteins on avian *Salmonella*-specific virulent plasmids, and the faeHI operon coding for fimbriae. So long as it functionally works in *Salmonella Gallinarum*, any gene cluster may be used.

The term "gene cluster," as used herein, refers to a population of adjacent genes on a chromosome or a plasmid that are commonly responsible for the same products. The genes in one cluster are under the regulation of common regulatory genes.

The inactivation of genes in bacteria can be achieved using various methods. For example, single or multiple nucleotides of an active site within a gene may be modified to decrease the activity of the protein expressed. Alternatively, an antibiotic-resistant gene or other gene(s) may be inserted into the gene of interest to prevent the expression of intact proteins. The most reliable method is to delete the entire sequence of a gene from the genome (Russell C B et al., J. Bacteriol. (1989); 171:2609-2613, Hamilton C M et al., J. Bacteriol. (1989); 171:4617-4622, Link A J et al., J. Bacteriol. (1997); 179: 6228-6237). In the present invention, entire sequences of the genes of interest are deleted to effectively promise the inactivation of the genes. For this, the one-step deletion method using lambda Red recombinase, known as a method of deleting gene clusters, developed by Datsenk K A et al., may be employed (Datsenko K A et al., PNAS, (2000); 97 (12):6640-6645).

With regard to the information of virulence genes to be deleted, nucleotide sequences of SPI-1 and SPI-2 were, obtained referring to the virulence gene sequences within the *Salmonella Gallinarum* chromosome (*Salmonella enterica* subsp. *enterica* serovar *Gallinarum* str. 287/91, NC 011274), disclosed by the NCBI. For the faeHI operon sequence, reference was made to the sequence of the *Salmonella Gallinarum* virulence plasmid gene (*Salmonella Gallinarum* virulence plasmid minor fimbrial subunit genes, AF005899). For the spvRABCD operon, the sequence of the same name gene of *Salmonella Typhimurium* LT2, which has highly homology with *Salmonella Gallinarum*, was consulted because its sequence is not disclosed in the NCBI. The sequencing of the spvRABCD operon of *Salmonella Gallinarum* was also performed with reference to the sequence of the corresponding gene of *Salmonella Typhimurium*.

Examples of the *Salmonella* virulence genes clusters include the SPI-1 gene cluster (SEQ ID NO: 1), the SPI-2 (SEQ ID NO: 2), the spvRABCD operon (SEQ ID NO: 3), and the faeHI operon (SEQ ID NO: 4) of *Salmonella Gallinarum* 287/91.

To prepare strains that, had definitely been rendered avirulent, all of the plural virulence gene clusters were deleted. To inactivate many gene clusters in one strain, the gene clusters may have been deleted sequentially.

In the present invention, a *Salmonella Gallinarum* strain in which only the SPI-2 gene cluster is inactivated (SG3-d2), a *Salmonella Gallinarum* strain in which both SPI-1 and SPI-2 gene clusters are integrally inactivated (SG3-d1d2) and a *Salmonella Gallinarum* strain in which all of the four virulence gene clusters (SPI-1, SPI-2, spvRABCD, faeHI) are integrally inactivated (SG3-d4). SG3-d2 is deposited under accession No. KCCM 11009P, SG3-d1d2 under accession No. KCCM 11010P, and SG3-d4 under accession No. KCCM 11011P.

Studies on the independent deletion of individual genes of the gene clusters have been reported (Hapfelmeier S et al., J Immunol, (2005); 174(3): 1675-1685, Brumme S et al., Vet Microbiol, (2007); 124(3-4):274-285, Desin T S et al., Infect Immun, July (2009); 2866-2875), but avirulent *Salmonella* strains developed by integrally inactivating two or more entire gene clusters had not been disclosed prior to the study of the present inventors. The *Salmonella Gallinarum* strain was named *Salmonella Gallinarum* SG2293-d2 when only the SPI-2 gene cluster is inactivated, and SG2293-d1d2 when both SPI-1 and SPI-2 were integrally inactivated. Further, it was named SG2293-d4 upon the inactivation of all of SPI-1, SPI-2, spvRABCD, and faeHI.

To ascertain the avirulence thereof, the strains prepared by inactivating virulence gene clusters according to the present invention were assayed for the efficiency of invasion into avian epithelial cells and for disease outbreak and mortality (%) upon infection into poultry. Preferably, the *Salmonella Gallinarum* strains in which the virulence gene clusters had been inactivated by transformation were allowed to invade avian epithelial cells so that invasion efficiency could be measured. Also, the strains were injected into brown egg layers to measure mortality.

In accordance with another aspect thereof, the present invention provides an avirulent *Salmonella*, strain for use in producing *Salmonella*-specific lytic bacteriophages and a method for producing phages using the same.

ΦCJ1 (US 20100135962), a *Salmonella*-specific phage, was used to examine the bacteriophage productivity of the avirulent *Salmonella Gallinarum* variants. The phage shows a specific bactericidal activity against *Salmonella Gallinarum* and *Salmonella pullorum*, belongs to the morphotype group of the family Siphoviridae B1, characterised by isometric capsid and long non-contractile tail, and has a total genome size of 61 kb and major structural proteins with a size of 38 kDa and 49 kDa.

The method for producing a bacteriophage in accordance with the present invention comprises culturing the avirulent *Salmonella Gallinarum* variants in a medium, inoculating a bacteriophage into the medium, and recovering the bacteriophage. In this regard, the phage may be produced briefly using a plate or on a mass scale using broth. In the case of production using a plate, a bacteriophage is inoculated at a suitable ratio into bacteria when the bacteria enter a log phase, mixed with top agar, and poured onto a plate. When phage plaques appear, the top agar fractions are collected and centrifuged, followed by filtering the supernatant to afford a phage stock. For mass production as a broth, a mixture of phages and bacteria is prepared in the same manner as in plate production, and incubated for 5 hours in fresh broth, instead of in top agar.

In accordance with a further aspect thereof, the present invention provides a pharmaceutical composition for the prevention of fowl typhoid, comprising the avirulent *Salmonella* strain as an active ingredient and optionally a pharmaceutically acceptable vehicle, and preferably a vaccine for the prevention of fowl typhoid, formulated with the avirulent *Salmonella* strain and optionally a pharmaceutically acceptable vehicle.

The term "pharmaceutically acceptable vehicle," as used herein, refers to a carrier or diluent which does not deteriorate the biological activity and property of the active ingredient and which does not irritate the subject. Preparations intended for oral administration may take the form of tablets, troches, lozenges, aqueous or oily suspensions, powders, granules, emulsions, hard or soft capsules, syrups, elixirs, etc. In regards to the oral forms such as tablets and capsules, the active ingredient may be formulated in combination with a binder such as lactose, saccharose, sorbitol, mannitol, starch, amylpectin, conjugate such as cellulose or gelatin, an excipient such as dicalcium phosphate, a disintegrant such as corn starch or sweet potato starch, or a lubricant such as magnesium stearate, calcium stearate, sodium stearylfumarate or polyethylene glycol wax. As for capsules, they may further comprise a liquid carrier such as fatty oil.

The composition of the present invention may be formulated into preparations for non-oral administration, such as subcutaneous injections, intravenous injections, or intradermal injections. For this, the composition of the present invention may be mixed with a stabilizer or buffer in water to give a solution or a suspension which is then formulated into unit doses such as ampules or vials.

As used herein, the term "vaccine" refers to a biological preparation that improves immunity to a particular disease by inducing the formation of an antibody upon injection into the body, a preparation containing an antigen, e.g., killed or attenuated forms of a disease-causing microorganism. Vaccines may be prepared from killed pathogens. There are also live vaccines, but with the virulence thereof attenuated. The *Salmonella Gallinarum* variants of the present invention have the same antigenic proteins as those of the wild-type, but are greatly decreased in virulence compared to the wild-type, so that they can be used as live vaccines prophylactic of fowl typhoid.

In accordance with still another aspect thereof, the present invention provides a feedstuff containing the avirulent *Salmonella Gallinarum*, and preferably a feed additive containing the avirulent *Salmonella Gallinarum*. When applied to poultry, the feed additive of the present invention serves as a live vaccine that prevents fowl typhoid.

The feedstuff of the present invention may foe prepared by mixing feedstuff with the *Salmonella Gallinarum* variant as it is or in the form of a feed additive. In the feedstuff, the *Salmonella Gallinarum* variant may be in a liquid or dry state. The dry state can be accomplished by various drying methods including, but not limited thereto, pneumatic drying, spontaneous drying, spray drying and freeze drying. In addition to the *Salmonella Gallinarum* variant of the present invention, the feedstuff of the present invention may further comprise a typical additive useful for improving the preservation of the feedstuff.

The feedstuff comprising the *Salmonella Gallinarum* variant of the present invention may be vegetable matter such as a cereal, nut, a by-product of food processing, millet, fiber, pharmaceutical by-product, a vegetable oil, starch, oil seed meals and cereal remnants, or animal matter such as proteins, minerals, fats, mineral oils, unicellular proteins, animal planktons and leftover food etc.

Examples of the feed additive comprising the *Salmonella Gallinarum* variant of the present invention include, but are not limited to, various agents for preventing quality deterioration and improving utility, such as binders, emulsifiers, preservatives, amino acids, vitamins, enzymes, probiotics, flavoring agents, non-protein nitrogen compounds, silicates, buffer, colorants, extracts, oligosaccharides, etc. Also, a mixing agent may be within the scope of the feed additive.

In accordance with still a further aspect thereof, the present invention provides a method for treating the *Salmonella Gallinarum* infectious disease fowl typhoid using the pharmaceutical composition.

The composition of the present invention may be administered to animals in the form of a pharmaceutical preparation to animals, or in the form of being mixed with feedstuff or water. Preferably, it is mixed in the form of a feed additive with feedstuff before administration.

So long as it allows the composition of the present invention to reach tissues or cells of interest, any administration route, such as non-oral, intraartery, intradermal, transdermal, intramuscular, intraperitoneal, intravenous, subcutaneous, oral or intranasal route, may be taken.

The treating method of the present invention comprises administering the composition of the present invention in a pharmaceutically effective amount. It will be apparent to those skilled in the art that the suitable, total daily dose may be determined by an attending physician within the scope of medical judgment. The specific therapeutically effective dose level for any particular patient may vary depending on a variety of factors, including the kind and degree of desired reaction, the specific composition, including the use of any other agents according to the intended use, the patient's age, weight, general health, gender, and diet, the time of administration, the route of administration, and rate of the excretion of the composition; the duration of the treatment; other drugs used in combination or coincidentally with the specific composition; and like factors well known in the medical arts. Typically, the composition may be administered at a daily dose of from $10^4$ to $10^8$ CFU once or in a divided dosage manner.

Hereinafter, the present invention will be described in more retail with reference to Examples. However, these Examples are for illustrative purposes only, and the invention is not intended to be limited by these Examples.

EXAMPLE 1

Screening of Target Genes to be Inactivated through Comparison of *Salmonella Gallinarum* Virulence Genes The first step of preparing avirulent avian *Salmonella* strains was the screening of target virulence genes to be inactivated. *Salmonella* Pathogenicity Island-1 (SPI-1), and *Salmonella* Pathogenicity Island-2 (SPI-2), both of which are type three secretion system gene clusters essential for the delivery of the pathogenicity of *Salmonella*, and spvRABCD and faeHI, both of which are genes on virulence plasmids, were determined as target genes, and the data base of the NCBI was searched for the nucleotide sequences of the target genes (*Salmonella enterica* subsp. *enterica* serovar *Gallinarum* str. 287/91, NC 011274). Because the nucleotide sequence of spvRABCD of *Salmonella Gallinarum* had not yet been disclosed, primers were synthesized with reference to the nucleotide sequence of the same name gene of *Salmonella typhimurium* (*Salmonella typhimurium* LT2 plasmid pSLT, NC 003277), which has high nucleotide sequence homology with *Salmonella Gallinarum*. As for the faeHI operon, the information of its nucleotide sequence was obtained from *Salmonella Gallinarum* virulence plasmid minor fimbrial subunit genes (AF005899).

EXAMPLE 2

Preparation of Avirulent Variants by Inactivation of Virulence Genes of *Salmonella Gallinarum* and by Integration of the Inactivated Sites 2-1. Inactivation of Virulence Genes of *Salmonella Gallinarum*

To delete TTSS-related virulence genes of the wild-type *Salmonella Gallinarum* (SGSC No. 2293) as determined in Example 1, the one-step deletion method using lambda Red recombinase, developed by Datsenko K A et al., (Datsenko K A et al, PNAS, (2000); 97(12):6640-6645), was employed.

A chloramphenicol resistant gene of pKD3 was used as an antibiotic marker for identifying insertion into a target site of chromosome. Using a pair of the primers SPI-1-P1 (SEQ ID NO: 5) and SPI-1-P2 (SEQ ID NO: 6) of Table 1, which correspond to 50 bp of 5' flanking region of the avrA and 50 bp of 3' flanking region of the invH gene, wherein SPI-1 comprising from avrA to invH is target for deletion, and a part of the chloramphenicol resistant gene of pKD3, respectively, a polymerase chain reaction (hereinafter referred to as "PCR") was performed [Sambrook et al, Molecular Cloning, a Laboratory Manual (1989), Cold Spring Harbor Laboratories], with pKD3 as a template. The obtained PCR product was gene fragment about 1100 bp long.

In this regard, a PCR EL premix kit (BIONEER) was used and 30 cycles of denaturation at 94° C. for 30 sec, annealing at 55 ° C. for 30 sec and elongation at 72° C. for 1 min was conducted. The PCR product was separated in 0.8% agarose gel by electrophoresis and eluted at a desired band size.

According to the method of Datsenko K A et al., the 1100 bp-long gene fragment was introduced into pKD46-transformed, competent wild-type *Salmonella Gallinarum*, which was then spread over LB plates containing chloramphenicol (30 mg/L), As for the resulting transformant, its gene was examined by PCR using a pair of the primers SPI-1-P3 (SEQ ID NO: 7) and SPI-1-P4 (SEQ ID NO: 8), which correspond to regions about 1 kb distant from both ends of the deletion target gene, respectively. The PCR product thus obtained was 3100 bp long, indicating that the SPI-1 gene cluster was inactivated.

The resulting strain was cultured at 37° C., a condition of removing the pKD46 vector, to select a strain that could not grow on an LB plate containing ampicillin (100 mg/L).

Subsequently, the antibiotic marker inserted into the inactivated gene cluster was removed by transformation with pCP20. The removal of the antibiotic marker was identified by PCR using the primers SPI-1-P3 & SPI-1-P4. The resulting PCR product was 2000 bp long, also indicating the inactivation.

Afterwards, the strain which was now free of the antibiotic marker was cultured at 42° C. (a condition of removing pCP20) to select a strain that could not grow on an LB plate containing ampicillin. The SPI-1 gene cluster-inactivated strain thus obtained was named SG3-d1 (*Salmonella Gallinarum* SG2293::ΔSPI-1).

SPI-2, spv, and fae gene clusters were also inactivated in the same manner as in the SPI-1 gene cluster. The resulting gene cluster-inactivated strains were named SG3-d2 (*Salmonella Gallinarum* SG2293::ΔSPI-2, Accession No. KCCM 11009P), SG3-ds (*Salmonella Gallinarum* SG2293::Δspv), and SG3-df (*Salmonella Gallinarum* SG2293::Δfae), respectively. Primers used for deleting genes and for identifying gene deletion are summarized in Table 2, below.

TABLE 2

| | |
|---|---|
| Primers for deletion of SPI-1 gene from chromosome | |
| SPI-1-P1 (SEQ ID NO: 5) | TTATGGCGCTGGAAGGATTTCCTCTGGCAGGCAACCT TATAATTTCATTAGTGTAGGCTGGAGCTGCTTC |
| SPI-1-P2 (SEQ ID NO: 6) | ATGCAAAATATGGTCTTAATTATATCATGATGAGTTC AGCCAACGGTGATCATATGAATATCCTCCTTAG |
| Primers for Deletion of SPI-2 Gene from Chromosome | |
| SPI-2-P1 (SEQ ID NO: 9) | ACCCTCTTAACCTTCGCAGTGGCCTGAAGAAGCATAC CAAAAGCATTTATGTGTAGGCTGGAGCTGCTTC |
| SPI-2-P2 (SEQ ID NO: 10) | ACTGCGTGGCGTAAGGCTCATCAAAATATGACCAATG CTTAATACCATCGCATATGAATATCCTCCTTAG |
| Primers for Deletion of spvRABCD gene from virulence plasmid | |
| spv-P1 (SEQ ID NO: 13) | GTGCAAAAACAGGTCACCGCCATCCTGTTTTTGCACA TCAAA ACATTTTTGTGTAGGCTGGAGCTGCTTC |
| spv-P2 (SEQ ID NO: 14) | TTACCCCAACAGCTTGCCGTGTTTGCGCTTGAACATA GGGAT GCGGGCTTCATATGAATATCCTCCTTAG |
| Primers for Deletion of faeHI gene from virulence plasmid | |
| fae-P1 (SEQ ID NO: 17) | TTACCGATATTCAATGCTCACCGCCAGGGAGGTATGC CAGCG GGACGGTAGTGTAGGCTGGAGCTGCTT C |
| fae-P2 (SEQ ID NO: 18) | ATGAAAATAACGCATCATTATAAATCTATTATTTCCG CC CTGGCCGCGCTCATATGAATATCCTCCTTAG |
| Primers for identificaion of SPI-1 gene deletion from chromosome | |
| SPI-1-P3 (SEQ ID NO: 7) | ATGTTCTTAACAACGTTACTG |
| SPI-1-P4 (SEQ ID NO: 8) | AGGTAGTACGTTACTGACCAC |
| Primers for identification of SPI-2 gene deletion from chromosome | |
| SPI-2-P3 (SEQ ID NO: 11) | TGTTCGTACTGCCGATGTCGC |
| SPI-2-P4 (SEQ ID NO: 12) | AGTACGACGACTGACGCCAAT |
| Primers for spvRABCD gene deletion from virulence plasmid | |
| spv-P3 (SEQ ID NO: 15) | GACCATATCTGCCTGCCTCAG |
| spv-P4 (SEQ ID NO: 16) | CAGAGCCCGTTCTCTACCGAC |

TABLE 2-continued

Primers for faeHI gene deletion from
virulence plasmid

| | |
|---|---|
| fae-P3 (SEQ ID NO: 19) | CAGGCTCCCCTGCCACCGGCT |
| fae-P4 (SEQ ID NO: 20) | CAGGCCAACTATCTTTCCCTA |

2-2. Integration of Type III Secretion System-Related Virulence Genes Inactivation To integrally inactivate the gene clusters in one strain, the SG3d1 strain was sequentially subjected to the inactivation of SPI-2, spvRABCD, and faeHI gene clusters, using a method similar to that of Example 2-1.

To begin with, PCR was performed using the primers SPI-2-P1 (SEQ ID NO: 9) and SPI-2-P2 (SEQ ID NO.: 10) for the purpose of inactivating the SPI-2 cluster gene, with pKD4 serving as a template, resulting a 1600 bp gene fragment. This PCR product was introduced into the SG3-d1 strain in which pKD46 vector retrained (Example 1-2), followed by spreading the bacteria over an LB plate containing kanamycin (50 mg/L). As for the resulting transformant, its gene was examined by PCR using a pair of the primers SPI-2-P3 (SEQ ID NO: 11) and SPI-2-P4 (SEQ ID NO: 12), which correspond to both flanking regions of the deletion target gene. The PCR product thus obtained was 3600 bp long, indicating that the SPI-2 gene cluster was inactivated.

The resulting strain was cultured at 37° C., a condition of removing the pKD46 vector, to select a strain that could not grow on an LB plate containing ampicillin (100 mg/L).

Subsequently, the antibiotic marker inserted into the inactivated gene cluster was removed by transformation with pCP20. The removal of the antibiotic marker was identified by PCR using the primers SPI-1-P3 & SPI-1-P4 in case of SPI-1 and the primers SPI-2-P3 & SPI-2-P4 in case of SPI-2. The resulting PCR product was 2000 bp long, also indicating that the inactivation had taken place.

Afterwards, the strain free of the antibiotic marker was cultured at 42° C. (a condition of removing pCP20) to select a strain that could not grow on an LB plate containing ampicillin. The SPI-1 and SPI-2 gene cluster-inactivated strain thus obtained was named SG3-d1d2 (*Salmonella Gallinarum* SG2293::ΔSPI-1ΔSPI-2, Accession No. KCCM 11010P).

In SG-d1d2 strain, spvRABCD and faeHI gene clusters were further inactivated. To this end, the spvRABCD gene cluster (the kanamycin-resistant gene of pKD4 was used as an antibiotic marker) was inactivated in the same manner as in the inactivation of SPI-1 in Example 1-2, while the inactivation of the faeHI gene cluster (the chloramphenicol-resistant gene of pKD3 was used as an antibiotic marker) was conducted in the same manner as in the inactivation of SPI-2 in the SPI-1-inactivated strain. As for the resulting transformants, their genes were examined by PCR using the primer set spv-P3 (SEQ ID NO: 15) and spv-P4 (SEQ ID NO: 16) for spvRABCD deletion, and the primer set fae-P3 (SEQ ID NO: 19) and fae-P4 (SEQ ID NO: 20) for faeHI deletion, which correspond to regions about 1 kb distant from both ends of the respective deletion target genes. The PCR products thus obtained were 3600 bp, 3100 bp long respectively, indicating that the spvRABCD and faeHI gene clusters were inactivated. The resulting strain was cultured at 37° C., a condition of removing the pKD46 vector, to select a strain that could not grow on an LB plate containing ampicillin (100 mg/L). The *Salmonella Gallinarum* strain in which all of the four gene clusters SPI-1, SPI-2, spvRABCD and faeHI were integrally inactivated was named SG3-d4 (*Salmonella Gallinarum* SG2293:: ΔSPI-1ΔSPI-2ΔspvRABCDΔfaeHI) and deposited under accession No. KCCM 11011P.

2-3. Sequencing of *Salmonella Gallinarum* spvRABCD Operon

Nowhere has the genetic information on spvRABCD of *Salmonella Gallinarum* (SGSC No. 2293) been disclosed yet. Its nucleotide sequence was analyzed in the present invention. For this, primers were synthesized as summarized in Table 3, below.

TABLE 3

| | |
|---|---|
| spv-S1 (SEQ ID NO: 21) | GGTCAATTAAATCCACTCAGAA |
| spv-S2 (SEQ ID NO: 22) | ACGGGAGACACCAGATTATC |
| spv-S3 (SEQ ID NO: 23) | TTCAGTAAAGTGGCGTGAGC |
| spv-S4 (SEQ ID NO: 24) | CCAGGTGGAGTTATCTCTGC |
| spv-S5 (SEQ ID NO: 25) | ACTGTCGGGCAAAGGTATTC |
| spv-S6 (SEQ ID NO: 26) | TTTCTGGTTACTGCATGACAG |
| spv-S7 (SEQ ID NO: 27) | TCCAGAGGTACAGATCGGC |
| spv-S8 (SEQ ID NO: 28) | GAAGGAATACACTACTATAGG |
| spv-S9 (SEQ ID NO: 29) | GTGTCAGCAGTTGCATCATC |
| spv-S10 (SEQ ID NO: 30) | AGTGACCGATATGGAGAAGG |
| spv-S11 (SEQ ID NO: 31) | AAGCCTGTCTCTGCATTTCG |
| spv-S12 (SEQ ID NO: 32) | AACCGTTATGACATTAAGAGG |
| spv-S13 (SEQ ID NO: 33) | TAAGGCTCTCTATTAACTTAC |
| spv-S14 (SEQ ID NO: 34) | AACCGCTTCTGGCTGTAGC |
| spv-S15 (SEQ ID NO: 35) | CCGTAACAATGACATTATCCTC |

The analysis result is given in SEQ ID NO: 3.

EXAMPLE 3

Assay of Virulence Gene-Inactivated *Salmonella Gallinarum* SG2-d4 for Avirulence by Measurement of Invasion Efficiency into Avian Epithelial Cell

*Salmonella Gallinarum* and *Salmonella pullorum*, which are unique *Salmonella* species due to the lack of a motile flagella, are specifically infected to avian cells and can invade other animal cells but at very low efficiency. In this example, an in vitro cell invasion assay was conducted (Henderson S C et al, Infect Immun, (1999); 67(7):3580-3586) on the avian epithelial cell line BAT (Budgerigar Abdominal Tumor), provided from M D. Lee, Georgia University. The avirulent *Salmonella Gallinarum* variants SG3-d1d2 and SG3-d4, developed by the above-described gene deletion method, were expected to invade the host cell with very low efficiency by reduced level of TTSS-related protein. A recent research review on the infection mechanisms of pathogenic microorganisms has it that even when only a specific gene of SPI-1 is deleted, the *Salmonella* strain shows a decrease in invasion efficiency into epithelial cells (Lostroh C P et al. Microbes Infect, (2001); 3(14-15):1281-1291).

In the present invention, TTSS-related gene deletion was proven to lead to a decrease in virulence by measuring the efficiency of the invasion of the avian *Salmonella* variants into the avian epithelial cell line BAT.

Invasion efficiency into avian epithelial cells was measured on 24-well plates in triplicate, and mean values of three measurements were given. The BAT cell line was cultured at 37° C. in DMEM supplemented with 10% fetal bovine serum, 1 mM glutamine, 100 IU/ml penicillin and 100 μg/ml streptomycin under the condition of 5% $CO_2$. The BAT cell line was seeded at a density of $2.5\times10^5$ cells/well into 24-well plates and incubated at 37° C. for 1~2 days in a 5% $CO_2$ incubator to form monolayers of cells. After distribution of the cell and incubation for one day, the culture medium was changed out with antibiotic-free DMEM. For comparison of invasion efficiency, wild-type *Salmonella Gallinarum* SG3 (SGSC: 2293), the virulence gene-inactivated *Salmonella Gallinarum* variants SG3-d1, SG3-d2, SG3-d1d2 and SG3-d4, and SG9R, which is a commercially available live vaccine, were employed, with the non-pathogenic *E. coli* MG1655 serving as a control.

After being primarily seed cultured, all of test bacteria were vigorously incubated for 4~5 hours in a main LB medium, and the cultures were diluted to $OD_{600}$=1.0. To 200 μL of the animal cells incubated in the antibiotic-free medium, 200 μL of each of the culture dilutions was added so that the bacteria were aliquoted at a concentration of $2.0\times10^8$ cfu/ml per well. The plates were incubated at 37° C. for one hour in a 5% $CO_2$ atmosphere to allow the bacteria to penetrate into the epithelial cells. Thereafter, the medium was aspirated off and the plates were washed with 1×PBS to remove remaining microorganisms. Then, the epithelial cells were incubated at 37 ° C. for 2 hours in the presence of 50 μg/ml gentamycin in a 5% $CO_2$ incubator to clear the microorganisms remaining outside the cells. The antibiotic was removed by washing with 1×PBS. To examine the microorganisms which succeeded in penetrating into the epithelial cells, the animal cells were lyzed for 15~30 min in 500 μl of 0.1% Triton X-100. The cell lysates were spread over LB plates and incubated overnight at 37° C. so that the microorganisms that had grown could be counted. To calculate the invasion efficiency, 200 μL of the microorganism culture with $OD_{600}$=1.0 was also incubated.

$$\text{Invasion Efficiency}(\%)=\text{Count of Microorganisms invaded to Cell}/\text{Count of Microorganisms within Culture Medium } (OD_{600}=1.0)\times100$$

The BAT cell invasion efficiencies of the four transformed *Salmonella Gallinarum* variants prepared by the inactivation of virulence gene clusters were calculated.

Of them, the variant in which only the SPI-1 gene, cluster, responsible for cell invasion mechanism, was inactivated, was decreased in invasion efficiency by 84% compared to the wild-type. The SG3-d1d2 variant with the deletion of both SPI-1 and SPI-2 and the SG3-d4 variant with the deletion of all the four gene clusters were found to decrease in cell invasion efficiency by approximately 89% and 91%, respectively, compared to the wild-type *Salmonella Gallinarum* (SG3). The variants of the present invention were also remarkably reduced in invasion ability, in comparison to that of the commercially available live vaccine Nobilis SG9R. These data demonstrated that the inactivation of TTSS-related gene clusters decreases the virulence of *Salmonella Gallinarum* (see Table 4 and FIG. 2).

TABLE 4

| | Strain | Property | Genotype | Index of Internalization (%) |
|---|---|---|---|---|
| Control Group | MG1655 | Avirulent *E. coli* | Wild type | 2% |
| | SG3 | Virulent *Salmonella Gallinarum* (Wild-type, SGSC No. 2293) | Wild type | 100% |
| | Nobilis SG9R | *Salmonella Gallinarum* Live vaccine (commercially available) | SG:: ΔrecA | 67% |
| Test Group (avirulent *Salmonella Gallinarum*) | SG3-d1 | Virulence gene-deleted *Salmonella Gallinarum* | SG:: ΔSPI-1 | 16% |
| | SG3-d2 | Virulence gene-deleted *Salmonella Gallinarum* | SG:: ΔSPI-2 | 34% |
| | SG3-d1d2 | Virulence gene-deleted *Salmonella Gallinarum* | SG:: ΔSPI-1/ΔSPI-2 | 11% |
| | SG3-d4 | Virulence gene-deleted *Salmonella Gallinarum* | SG:: ΔSPI-1/ΔSPI-2/Δspv/Δfae | 9% |

(SG3 100% = 0.36% invasion efficiency in practice)

The avirulence of *Salmonella Gallinarum* variant SG3-d4 was confirmed in vitro test which shows extremely low in invasion efficiency into avian epithelial cells, as was reconfirmed in animal tests and the results are given in Example 4.

EXAMPLE 4

Assay of *Salmonella Gallinarum* SG3-d4 for Avirulence by Measuring Mortality of Chickens The Research Institute of veterinary Science, Seoul National University, was entrusted with this assay. One-week-old brown egg layers (Hy-Line chicken) were employed in this assay, and they were divided into many groups of 10 which were separated in respective chicken houses before infection with pathogens. No vaccine programs were used on the experimental animals after they hatched.

Five avian *Salmonella* strains including the wild-type *Salmonella Gallinarum* SG3 (SGSC: 2293), the virulent gene cluster-inactivated *Salmonella Gallinarum* SG3-d2 and SG3-d4 (identified to decrease in virulence by in vitro invasion assay), the commercially available live vaccine Nobilis SG9R, and the non-pathogenic E, coli MG1655 were employed in the in vivo assay.

After being primarily seed cultured, the five strains were vigorously incubated for 4~5 hours to $OD_{600}$=1.0 in a main LB medium, and the concentration of each of the cell cultures was adjusted to $1.0\times10^8$ cfu/ml. The bacteria was subcutaneously injected at an adjusted dose into the chickens which were the monitored for two weeks for mortality. Subsequently, the chickens which were alive were autopsied to examine lesions and to isolate bacteria.

For the two weeks after artificial, infection of the pathogens ($1.0 \times 10^8$ cfu/mL), the chickens infected with *Salmonella. Gallinarum* (SG3) were observed and showed typical external syndromes such as low motility, blue diarrhea and low uptake of feedstuff, and looked to be dying. The mortality was not high, but an autopsy disclosed lesions in almost all the chickens.

In contrast, the chicken group infected with the *Salmonella Gallinarum* variant (SG3-d4) the avirulence of which was proven by in vitro invasion assay were observed to actively move and not die although some of them had diarrhea during the two weeks. Also, they were found to have almost no lesions in the autopsy. Therefore, the *Salmonella Gallinarum* variant of the present invention was again proven to have greatly decreased virulence. The chicken groups infected with the SG3-d2 variant in which the gene responsible for primary invasion into host cells remains intact while the SPI-2 gene involved in systemic infection and survival over phagocytosis is inactivated, or with the SG3-ds variant in which the spv gene known to participate in pathogenicity is inactivated, were observed to have low or no mortality (%). Thus, even the inactivation of single gene clusters had a great influence on the reduction of pathogenicity (see Table 5).

TABLE 5

| | Strain | Property | Genotype | Mortality (%) | Frequency of lesions in live birds (%) |
|---|---|---|---|---|---|
| Control Group | MG1655 | Avirulent *E. coli* | Wild-type | 0% | 20% (2/10) |
| | SG3 | Virulent *Salmonella Gallinarum* (Wild-type, SGSC No. 2293) | Wild-type | 20% | 88% (7/8) |
| | Nobilis SG9R | *Salmonella Gallinarum* Live vaccine (commercially available) | SG:: ΔrecA | 0% | 40% (4/10) |
| Test Group (avirulent *Salmonella Gallinarum*) | SG3-d1 | Virulence gene-deleted *Salmonella Gallinarum* | SG:: ΔSPI-1 | 40% | 17% (1/6) |
| | SG3-d2 | Virulence gene-deleted *Salmonella Gallinarum* | SG:: ΔSPI-2 | 10% | 0% (0/9) |
| | SG3-ds | Virulence gene-deleted *Salmonella Gallinarum* | SG:: Δspv | 0% | 20% (2/10) |
| | SG3-d4 | Virulence gene-deleted *Salmonella Gallinarum* | SG:: ΔSPI-1/ΔSPI-2/Δspv/Δfae | 0% | 10% (1/10) |

According to autopsy findings, the liver and spleen were swollen and weakened, with the significant frequency of greenish brown or bluish green liver lesions, in the chicken group infected with the wild-type *Salmonella Gallinarum* (SG3). Like the commercially available live vaccine Nobilis SG9R or the non-pathogenic *E. coli* MG1655, however, the virulent gene cluster-inactivated variants of the present invention (SG3-d1d2 and SG3-d4) were found to produce almost no lesions, and were demonstrated to be harmless to chickens.

EXAMPLE 5

Comparison of the Productivity of ΦCJ1 Bacteriophage Specific to *Salmonella Gallinarum* Variants Ultimately, the development of avirulent *Salmonella* stains is to apply to the production of *Salmonella*-specific lytic bacteriophages. The *Salmonella* variants prepared in Example 2 were proven to have greatly attenuated virulence in Examples 3 and 4. Finally, ΦCJ1 (Korean Patent Application No. 10-2008-121500/US20100135962), which specifically infects avian *Salmonella*, was used to examine a difference in bacteriophage productivity between the wild-type and the avirulent *Salmonella Gallinarum* variants.

The avian-specific bacteriophage ΦCJ1 was cultured on a mass scale, with the wild-type *Salmonella Gallinarum* strain (SG3) or the variant serving as a host cell. For this, each bacterial strain was cultured to an $OD_{600}$ of 0.5 ($2.5\times10^{10}$ colony forming units (cfu)) in 50 ml of LB broth in a flask with agitation. ΦCJ1 was inoculated at $1.25\times10^9$ pfu (plaque forming unit) to form an MOI (multiplicity of infection) of 0.05, and allowed to stand for 20 min at 37° C., followed by additional incubation at 37° C. for 4 hours. Chloroform was added in an amount of 2% of the final volume and shakes for 20 min. After passage of the supernatant through a 0.2 μm filter, the titer of ΦCJ1 was counted.

ΦCJ1 was produced at a titer of $6\times10^{11}$ pfu/ml from the wild-type strain (SG3) and at a titer of $8\times10^{10}$ pfu/ml from the avirulent *Salmonella Gallinarum* variant (SG3-d4). These data demonstrated that the avirulent variants prepared by inactivating virulence gene clusters have no problems with infection with bacteriophages and can be used as host cells for producing bacteriophages (see Table 6). In addition, ΦCJ2

(US 20100158870) and ΦCJ3 (US 20100166709), which were both developed by the same applicant, were produced using the variant as a host cell. The host cell was found to allow the production of ΦCJ2 at a titer of approximately $2\times10^{10}$ pfu/ml and ΦCJ3 at a titer of approximately $5\times10^{9}$ pfu/ml. Like ΦCJ1, ΦCJ2 and ΦCJ3 were produced from the variant of the present invention, without significant difference from the wild-type.

TABLE 6

| | Strain | Property | Genotype | Production Titer of ΦCJ1 (pfu/ml) |
|---|---|---|---|---|
| Control Group | SG3 | Virulent *Salmonella Gallinarum* (Wild-type, SGSC No. 2293) | Wild type | $6 \times 10^{11}$ |
| Test Group (avirulent *Salmonella Gallinarum*) | SG3-d4 | Virulence Gene-Deleted *Salmonella Gallinarum* | SG3::ΔSPI-1/ΔSPI-2/Δspv/Δfae | $8 \times 10^{10}$ |

As described hitherto, the avirulent *Salmonella Gallinarum* variants, prepared by inactivating virulence genes, according to the present invention are useful as host cells for effectively producing *Salmonella*-specific lytic bacteriophages on an industrial scale with the advantage of cost saving. The avirulent *Salmonella Gallinarum* variants simplify the purification process taken to remove toxicity after bacteriophage production, thus greatly reducing the production cost and solving the safety problem of the products. In addition, the variants can be used as live vaccines that guarantee higher immunological effects and safety than do conventional vaccines.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating *Salmonella Gallinarum*-infectious fowl typhoid in animals by administering an avirulent *Salmonella Gallinarum* as an effective ingredient, wherein the avirulent *Salmonella Gallinarum* comprises an inactivated gene cluster of *Salmonella* Pathogenicity Island-2, wherein the inactivation of the gene cluster is carried out using a method selected from the group consisting, of modification of single or plural nucleotides in the gene, deletion of single or plural genes, insertion of an exogenous gene into the genes, deletion of all of the gene clusters, and a combination thereof.

2. The method of claim 1, wherein the avirulent *Salmonella Gallinarum* comprises a deleted gene cluster of *Salmonella* pathogenicity island-2 of SEQ ID NO:2.

3. The method of claim 2, wherein the avirulent *Salmonella Gallinarum* is deposited under accession No. KCCM 11009P.

4. The method of claim 2, wherein the avirulent *Salmonella Gallinarum* further comprises deleted gene clusters of *Salmonella* Pathogenicity Island-1 of SEQ ID NO: 1, spvRABCD of SEQ ID NO: 3, and faeHI of SEQ ID NO: 4.

5. The method of claim 4, wherein the avirulent *Salmonella Gallinarum* is deposited under accession No. KCCM 11011P.

6. The method of claim 1, wherein the avirulent *Salmonella Gallinarum* further comprises inactivated gene clusters of *Salmonella* Pathogenicity Island-1, spvRABCD, and faeHI.

* * * * *

SEQUENCE LISTING

<160> NUMBER OF SEQ ID NOS: 35

<210> SEQ ID NO 1
<211> LENGTH: 34934
<212> TYPE: DNA
<213> ORGANISM: Artificial Sequence
<220> FEATURE:
<223> OTHER INFORMATION: Salmonella pathogenicity island-1

<400> SEQUENCE: 1
ttacgattta agtaaagact tatattcagc tatccttttt ttatgagcgg atatagagag 60 tttttatcg tttagcataa cggcattgtt atcgaatcgc tcataaagcg tttcattctt 120
tttgtttact atactgcttc ccgccgccgg attggcctcc acatattcat ttaatcgttg 180
tacgccttga gtatgtttgt aaaaactcac cggcagataa cggtctgctt tatcggacgg 240
gagaaaaggt tcttcaccac acagacgttc acaaatatta tcttcatgaa tttttactaa 300
gttcataaat tcaagctgaa gttttttggc gagcgccagg ctaaaaatac cgcattcaga 360
agagcttcgt tgaatgtcca gctcgaccat agcaaaataa caatcaggca gttgttcacg 420
ttcaagagct gctttggtcc tcaacgccag taaagcaggt ccaaaagcgc tacacgctgc 480
tggttcgaac aaaatcaccg atgtctttcc gtccataact ctaaaatcga cgactgaaat 540
atggatacct gaacttccca tatttacgag aaatcgggca gattcaacgc cttccattct 600
ggtctccttt atagaggaaa caagctcatg gactgacata acaaatttaa gatttaactc 660
tggatacttc ttattggcct gtgcaacaag aaaaggcatc atttcgagat cggtttcctc 720
gtaactgata tgaatccagc tgccatctat aatttcactt tccagacgct caacaataca 780
ggtcaatgct tcggtgttta gctccccgct gacgtcaggc tgaggcgata aactcgcccc 840
catattacga gtcgtaggac ttagcatact tttccctcca catgatagct cctgcaccga 900
aaatatcatc tttaactttt cagattcaat atattgcctg caaaaatatg cctcaatgat 960
tgagccaggc taccaaccac ctccggatga ttatatataa gaattactac tcaaaaaatc 1020
ttttttataa taaaagctca acacatggtc ataaatgata aaaaatattt taattcattc 1080

```
ctaccgcaat cggtaacgcg caattatcgt caggtacagc agggttatgt gcaaaagcag    1140
tgcgctgtaa atgcgcgtct agtttcagtc cccggaacag cgatagcggt gaagagtcca    1200
tccccaaacg atacataacc ttcttacgat aaatactgac ggttttgtt  cccagaccaa    1260 attttttcgc cagttcaatt gccggatgtc cggaggataa taatatcagc agcgcatatt    1320
tcgcctgcgt gacaccggga ggtagattcc accaggcgta ttgattgata ttaaacaata    1380
cctcttccgg cgtctcgccg gcattaaaag catacgtagc agccacggtt ttcttttgtg    1440
gcctgtggca gaaacgcagc caggcttccg gaagacggag cttctctcgc tccgagcgga    1500
tagcgcagga tagttcgtct tttaaaacat aatccataac gccaaaatat tgcagcacac    1560
agcgatcgat ataatacaag cgatctgcca ctaccaaaac tttacggttc tgcaaccgcg    1620
tcagcaacgc atgaaaaaga taaacatgct catgcgggtt caaagctaaa atcagcccgg    1680
cgtccggcat atcggataga gaatgcaaaa gtgcggttaa tgagttacac gttttaacgc    1740
acttttccgg atattttgc  ttaaaaatag actgaagggc ataacaatta gtccagttaa    1800
taccgtatat aattacattt ctcatttatt tatccttttt tgaaaactga ccacagcttc    1860
ggtaatgatt tttcttcctg ggcgactact gcgcaagtag ataacgcctt cttactacaa    1920
aggtaataag accagatacg ttattacatg cgcaatgtcg ttaccgaaat gaattccttt    1980
tacaaatctg ataatgatta aatttactgt tttactttac tgtaatctct tagagtacaa    2040
cgattgcccg gcgcctggtg gccatgtatg tctgacaatg aacgctttcg attcccttc    2100 attaactaca tatcactggt gtagcgatac tgaaatatac actacgatta aaaaaatatt    2160
tggtatctgt aacgcaaaca gatagtaacg tttaaaataa tttcacaaat caatggttca    2220
tcgtacgcat aaagctaagc ggtgtaatct taaaatgccg tttaaaaata gcgataaaat    2280
aagaaggcgt atcatagcca cacatcgtcg cgacttgtga atatttcca  gcccccatac    2340 gtaataattt tatagcctga ttcatacgag catctaggta tattttgcta aaactcacct    2400
cttcagcggc cagttttcgc ttcagacttg atacgctcat aaacagcttt cccgccacct    2460
cagcctgtga ccatttgcgg gtgagatcgc tgataataat gttataaact ttctcttttg    2520
tcgtaatttt tattgctcgc tcaaggaaat caaacccacc gggcttacgt acaaatgccg    2580
atataagata catcaatgag aaatatgaat aatcatgatc atcaatactc acattactac    2640
aaacccgtgg acatgccaca ccatgcaaaa tagagtcaaa agtatcactc atccctggca    2700
acaagtccgc atgaaaaaaa tactttggtt tcgttttaa  tgatagctct cgatcattat    2760
agtttcttgt actgtaaaaa actttgtaga attttttgcat taagtcatag gaaacttcca    2820
gtgaagaaaa atcaatatgc ccttctattt cgctcatact aagcgtgatt gtttgatctt    2880
tttccaataa aaataaacac ggcgcagatt gttcgatgaa ctccccaaat tcgttttcaa    2940
ttcgcaaact gcctttatta agtttaaaca ataagcagtt tgcgacataa tagtctctta    3000
cgtcagctaa tccatttatt aatggaaatt tgttcggctg ttgaaggtga ttattgctaa    3060
tggcctcaac tgatttattc attgaaggca ataccatatt ttatcctgtg tgctataagg    3120
aactcaaaat cgttatattc ttataaacaa ataattaaaa ctcacagaga tgatttaaat    3180
ccgatttttt tattattata gccaataatt acattccaac gcgcgttcat ttcgtcacaa    3240
aaagataccc ttacaaactt tatgcacaat tttgtaatga aagcttacaa tattaatata    3300
atcatttcag aataaaacgg ctggcagaca tcttaataat ccatatacat caataagata    3360
gacacactgg catggtgcat tttctgcatt atttgctgat atatacacca taccttatca    3420
caaatcgcca gcaatggggg ttcaccagtc aattgcctct ttgttttccc cgcccgataa    3480
```

```
aataatctcc tgcatccagg aggtcatttg tgactgtgcg ttcattgtac caactaatac    3540
cccgtttaaa gcctcatata aatgggtgcc cggttcaact tttgctaaca tgttttgtag    3600
catagccgtt tgctgctcaa aagaaacaaa agccgaatca ccactgttag gatctttgaa    3660
ggcattcatc tcttgataaa tgctatcttt aagcgtttca gaagaggctg actcaggaag    3720
cgccagaagt cgttggtaga atgcatcata aagatcaacg tcgccgccat tgcttaaagg    3780
cgcgctatcc acattattca gcatagcggc cctggcactc aacgaaacca cacccgtcgc    3840
ttcagtatct gctgtcggga ccaaataaga agtcggaatc gtacccggta tcaccttata    3900
acctccgctt gcgttttgt cttccattca tcaataagtg cgttaatggc gttatcagaa    3960
attgtccggc agtcttgtgg aagttcatca agatgatgct taatgacgcc tactgccgtt    4020
tcaacaaatt gttcaggtga aaattctgcg atctgatcgc cgcaactcat gataaagcgc    4080
tgttcctgat gatatttaag attaaaagtg cctggccagt tctccataag caacaccatc    4140 agttttggt gatcttttt cgcattaact ggcagtgtta aaaaagttg ccctcaggc        4200 ttatcgaaat ccttagcca ctcatccagg acggttaaaa gcgtttcggg atggtcgacc    4260
gcagctgaaa ataactcgcg ggcataaatc tgtattttt ccatccactt ccaggccatt    4320
gtctgattat cagtaagata agcggcgacc tgctgtaacg cgtctatcat tccctgctcg    4380
taaccttcct gataggcgta catccgcaag gtctttgcct cttcttccgc ctctcgcaaa    4440
atacgcttag cccgttgatg cgcctgctgt tctaatcttt caatagagaa ataacgttcc    4500
agcgttttac gctttatcag tatccctca acaggcgaaa gcgggacgg tattgggata     4560 ttttgagca tattgtaagg ccagtagcaa aattgacatt tctacagcat cctgcttcaa    4620
tgcctcctca ataatgggag gaaaaagcaa aggaaacgc tgtgctaaag attcaggtaa    4680
aaattcattt agggcattta actgtgcata cccgacgcta agtaaaaacc ggtgattcgg    4740
cgccttattg cagacagata aacttgttcc ctgatgcatt gccaaaaatg cttgcgccca    4800
atccggcagg ccaagcaagg ctccctgcct tgccagatcg gctctcagtt tatggcaacc    4860
gagtaaatac gctacctgcg gcagtcggcg ccactgacgc agccacagct gcgtcagtga    4920
gttttgaata cactccttt ctccgttctt aagccgccat gccgcagta ttaactcatt     4980 tgccgccgcc ctggcggcgg gtctgacaat catttccggc gctatctgca accgctgagg    5040
atggatatac gataacggat caaaaatgat tctttgccag ataatgggta atggctgcct    5100
attcatttga cgatttcgcc ttatcatcag ccgttatgcc tttcttattg cgggcataat    5160 ggttttgta ataccagacg ccaaagcctg ctgacatcac ggataacaaa ataatcaaca    5220
caatccaact ggttgcaaaa gaattacgtt ttactggtgt gccgggagcc tgtaattggg    5280
catcagaacg ttctgacaac acaacagaaa tgttgtcata atccacatcg gcaaaactat    5340
tctttaagaa acgcttgata tcgctgatct gatgcgcaag cggcgaacct cgttcatata    5400
cggctaatgc cgacagatga acaggttttg gcggacggcc attttcacca gcatcaatat    5460
cataactaat atggaccctg gcggagagca cgccctccat cgtctgtaat gactgttcca    5520
gtcgctgttc aatagccgaa tataacctgg ccttttcagc tcgcggagac gataccagcg    5580
aatccgccgg gaacatctgc gctatttcca cccgtggccg gggaggaagc tgataagttt    5640
taatccagta caccgcagcg gtaaaatcag gctcagcaac ggtaatgcta tagcccaatt    5700
ttccgctatc aattttattc gcctctatat tgtgcatttg cagaacggca atgacctcat    5760
tagcctgttc ctggtccagt cctttaaaa gatccttatc cttacagccg gcaagggtca    5820
ttaccagcag aaaggtatat agatatcgac gaatcatgag cgtaatagcg tttcaacagc    5880
```

-continued

```
cccgactcct ttacgagtaa gggtacttac catagaaaca tacaggttat aatctgaaat    5940
catctcttgc gaaatagcca gctctttagg atccgtcacc agattagggt cctcaatcct    6000
gttggtaatc gtctgtttat ccacagccgt ggcaatcgcc gaaccagaaa agcctggag    6060 tagccggtca tccagcgaga caatgtccgt ctccatagac ctgatattga ccgcctgccc    6120
tataacggca ttctctggga caatagttgc aatcgacata atccacctta taactgatta    6180
acggaagttc tgaataatgg cagcatcaat atccttaaag acttttaccg tgttcgattg    6240
cgcgttacgg tacaagttat attccgagag cttactctga tacgccgcca gtagcgccgg    6300
atcggagggt tttgctgcta atttatccag cgcctctgtt acctgcgttt gtagattatc    6360
aacgcccgta tcaaattttg ctgagacgtc atccagatag cctgaccaag gtgttgccat    6420
aatgacttcc ttatttacgt taaattaaag tgggcttggg aaataccaat ggcctgggct    6480
cattttgata taaccttccg ccccgtactg aaatgagcgc cccttgagcc agtcatcttt    6540
taattcgatc gcaaactgca catagcgtcc tccccatgtg cggtaatagc tatcgacaaa    6600
ttgacgggct ctgagtattt ctacatcatc gagcgccccc tgaataacaa acgttacgcc    6660 cccctttatga ttcctgcggg aataaggtaa cgcctgctgt tttagccccg cttccgcctg    6720
gcctgctgcg gtaacatcgt ccatcaacgt gatgttaacc gaatccgcgt aaggcattag    6780
cgctctcagc ttttgactta acatctcgag ctctttcttg ctcatcgtgt ttcgctggcg    6840
gcttagccag aaaacgggtt tacgcggctc atcgaaatga atccgataat aagccagctg    6900
cggataatag gtatccagcc agatagagat acgcttattt tcttcgtttt cgttaatcac    6960
tcgcgcattt ttatcataat cgcccctcgc taaaacctga cgagcccaca gcgtatctct    7020
ttcattttgc gcagcgacat agagcatttt gtcccggcct ggcaacacct gaaaacgctc    7080
cttctcctgc cccaataacg aatcgagctc tgcggcctgc cgctgcggcg agttaagtat    7140
ccataacgtc cccacagtcc caattcccaa tataaaaaac ccggccagtg ctgctacaat    7200
tccgttttta aaacgcggct cgttcttttt tgcagacgtt tctaacttct caggctgctc    7260
gggcacccac ggctcgcttt ccgggcgaat caggataagc aattcaccga cctgtattgg    7320
cgtatttaat tgcaccgaac gagattcaga atttccttct ttcagctcat ggagtataat    7380
ttcggtcgta tccgtatcca cctggatttc aaaatttact ccgccatggt ccagcgggat    7440
aaaaaagcta tcggcaggta tatcagggag ttggcctgaa gcagtgagcg catcactctg    7500
acctaccaca aagagtgttc ggcctgtcag caatggaaac tcacagccgt tcagtgagct    7560
gttaagtaat cgaactatgt atggcccagg gcttgttatc gtcttctctt ttgatgtttc    7620
catatatact gttagcgatg tctgtcgttc tcgatagcag cagattaccg cacaggacac    7680
agggattcct gatgaaaata gaatgaaaag tgagaaataa aatcaattta ttctgtataa    7740
tgcgtctcaa cacatattaa aagaaccatc atccccattg gggcttaaac tactgtagat    7800
aaattaccca aatttgggtt cttttggtgt aacaatcaga ccattgccaa cacacgctaa    7860
taaagagcat ttacaactca gatttttttca gtaggatacc agtaaggaac attaaaataa    7920
catcaacaaa gggataatat ggaaaatgta accttttgtaa gtaatagtca tcagcgtcct    7980
gccgcagata acttacagaa attaaaatca cttttgacaa atacccggca gcaaattaaa    8040
agtcagactc agcaggttac catcaaaaat ctttatgtaa gcagtttcac tttagtttgc    8100
tttcggagcg gtaaactgac gattagcaat aatcacgata cgatttactg tgacgaacct    8160
gggatgttgg tgctcaaaaa agagcaggta gttaacgtga cgcttgaaga ggtcaatggc    8220
cacatggatt tcgatatact cgagataccg acgcaacgac ttggtgctct ctatgcactt    8280
```

```
atcccaaacg agcagcaaac caaaatggcg gtacccacag agaaagcgca gaaaatcttc   8340
tatacgcctg actttcctgc cagaagagag gtatttgaac atctgaaaac ggcgttctcc   8400
tgtacgaagg atacaagcaa aggttgcagt aactgtaaca acaaaagttg tattgaaaat   8460
gaagagttaa ttccttattt tctgctgttc ctgcttactg cttttctccg actcccggag   8520
agttatgaga tcatccttag ctcggctcag ataacgttaa aggagcgcgt ttacaacatt   8580
atatcttcgt cacccagtag acagtggaag cttacggatg ttgccgatca tatatttatg   8640
agtacgtcaa cgctcaaacg gaaacttgca gaagaaggta ccagctttag cgacatctac   8700
ttatcggcaa gaatgaatca ggcagcaaaa cttttacgca taggcaacca taatgttaat   8760
gctgtagcat taaaatgtgg ttatgatagc acgtcctact tcattcaatg tttcaaaaaa   8820
tattttaaaa ctacgccatc gacattcata aaaatggcga accattaaca tttttttgtat  8880 ctgtcactta agtaaagatt tttattaaaa ttgtaataat ttaaaattca gactgcgcat   8940
taacacgctc tatcaggatg ggaggctatt caatatcatt gttctgtccg gaagacagct   9000
tatactgata tctctggtaa tttaaagtaa ggctgattat ataacacgat ttttgtgaac   9060
ttgtcatcgc tatgatgact ggtaaaacga tattgcctta ttcacagcgt aagaattcgt   9120
ccagatgaca ctatctcctt ccggctttaa ccctgtggat taaggccggc atttttattca  9180 tatttataca tcatccgttc cctctgagaa ctatttgcct gaacggttta taccgaaaca   9240
gtcacgcttg ttagctttct gccaggcata cctcctctct tcctcctgat atcgatataa   9300 tgcctgggc cagcctgagg atgatactgc tcataaaccc cctgcctttt tgacgctata   9360
actgaaggga gtaaagaaaa gacgatatca ttattttgca aaaaaatata aaaataagcg   9420
caccattaaa aacagtcttt catttatatt ttggaaccta agacaaatta cactcttaaa   9480 cttttcaacga atggtcattt agtggaaatc ttcgagaaaa atggttctga tggtgtaatt   9540
atcagaccat taaccatgaa gatataataa gcagcattta cacccaaaa aaatgcagta   9600 agatagctac aaaactaatc tctattgcaa tgaggccaag ttaaatatgt aaatatttag   9660
atgccaggcg ctgactctct ctgcaccagg atatacggca gcgtccattc gataatcacg   9720
gttagttata acaatattat taccaacatg tcagttattt aaagcacagg cataagctaa   9780
ataatcaaat gttaaaaaca tataaacccg agcccgtaga atatgacatt aagctcataa   9840
taaaagctca acctgaccgt tagtactaac agcagaatta ctgaaacagt agattctatc   9900
ctaacgactt gtattagtta ttataacttt tcaccctgta agagaataca ctattatcat   9960
gccacatttt aatcctgttc ctgtatcgaa taaaaaattc gtctttgatg atttcatact  10020
caacatggac ggctccctgc tacgctcaga aaagaaagtc aatattccgc caaaagaata  10080
tgccgttctg gtcatcctgc tcgaagccgc cggcgagatt gtgagtaaaa acaccttact  10140
ggaccaggta tggggcgacg cggaagttaa cgaagaatct cttacccgct gtatttatgc  10200
cttacgacgt attctgtcgg aagataaaga gcatcgttac attgaaacac tgtacggaca  10260
gggctatcgg tttaatcgtc cggtcgtagt ggtgtctccg ccagcgccgc aacctacgac  10320
tcatacattg gcgatacttc cttttcagat gcaggatcag gttcaatccg agagtctgca  10380
ttactctatc gtgaagggat tatcgcagta tgcgcccttt ggcctgagcg tgctgccggt  10440
gaccattacg aagaactgcc gcagtgttaa ggatattctt gagctcatgg atcaattacg  10500
ccccgattat tatatctccg ggcagatgat acccgatggt aatgataata ttgtacagat  10560
tgagatagtt cggggtaaag gttatcacct gctgcaccag gaaagcatta agttgataga  10620
acaccaaccc gcttctctct tgcaaaacaa aattgcgaat cttttgctca gatgtattcc  10680
```

```
cggacttcgc tgggacacaa agcagattag cgagctaaat tcgattgaca gtactatggt   10740
ttacttacgc ggtaagcatg agttaaatca atacaccccc tatagcttac agcaagcgct   10800
taaattgctg actcaatgcg ttaacatgtc gccaaacagc attgcgcctt actgtgcgct   10860
ggcagaatgc tacctcagca tggcgcaaat ggggattttt gataaacaaa acgctatgat   10920
caaagctaaa gaacatgcga ttaaggcgac agagctggac cacaataatc cacaagcttt   10980
aggattactg gggctaatta atacgattca ctcagaatac atcgtcggga gtttgctatt   11040
caaacaagct aacttacttt cgcccatttc tgcagatatt aaatattatt atggctggaa   11100
tcttttcatg gctggtcagt tggaggaggc cttacaaacg attaacgagt gtttaaaatt   11160
ggacccaacg cgcgcagccg cagggatcac taagctgtgg attacctatt atcataccgg   11220
tattgatgat gctatacgtt taggcgatga attacgctca caacacctgc aggataatcc   11280
aatattatta agtatgcagg ttatgtttct ttcgcttaaa ggtaaacatg aactggcacg   11340
aaaattaact aaagaaatat ccacgcagga ataacagga cttattgctg ttaatcttct   11400
ttacgctgaa tattgtcaga atagtgagcg tgccttaccg acgataagag aatttctgga   11460
aagtgaacag cgtatagata ataatccggg attattaccg ttagtgctgg ttgcccacgg   11520
cgaagctatt gccgagaaaa tgtggaataa atttaaaaac gaagacaata tttggttcaa   11580
aagatggaaa caggatcccc gcttgattaa attacggtaa aatctgagag aggagatatg   11640
cattattttt ttatcatcgt aatctggttg cttagcataa atacggcatg ggctgattgc   11700
tggcttcagg ctgaaaaaat gttcaatatt gaatccgaac tactttacgc tatcgcccag   11760
caggaatcgg cgatgaaacc tggcgccatt ggtcataacc gagatggttc aaccgatctt   11820
ggcctgatgc aaattaacag cttccatatg aaaaggctga aaaaaatggg gattagtgaa   11880
aaacagttgt tacaggaccc ctgcatttct gtcattgtgg gcgcttccat tttatcagat   11940
atgatgaaaa tctacggtta tagctgggag gccgttggcg cttataatgc cgggacgtcg   12000
ccgaaacgat cggatataag gaaacgttat gctaaaaaaa tttgggagaa ttacagaaaa   12060 ttaaaggaa tgtcagcaga agagaaaaac aaaagacttt ctatcgcgtc aaacaaataa   12120
ttatacagaa atagcttact ttcagatagt tctaaaagta agctatgttt ttatcagcgt   12180
gccgtcgtca taagcaactg ggcttgcatt gcttttagtt gtacaaactg tgaggcgtct   12240
tccagcattc tattgttccg tgaattccgg aaatctgcac gtacctgctc cagattacta   12300
tgaggattat ccttaagtac aagggccgcc gccatcgttc cggttctccc cactccgccc   12360
agacaatgaa tcatcggtaa atgcttatct gatgaactac gccccggcgc gccattttgg   12420
ttactatttt tcaccctatc cgccaggtat tctaactgat ccgtagacgg taacggctgg   12480
tgatctggcc aatttttcac atgcaatacc gggattgtat accgcttttc cccgcaggac   12540
agttgcatat tgtattggtc tatcgcttct ccctgactgg ctgagctcac ttttttggctg   12600 ttggtatgca cctcgccaaa ggtgtagctc cctctgaaat agggtggtaa ttgttttgcc   12660
tgcatctgat cttccgacgt taacaccacc aggcatgagc attcttttc aagaagcatt   12720 ttcatatgcg ctgccagcgc atccggcgta ttttttgggt acgaaccggc taatgccaca   12780
ggcttaccgt caaaagttaa cgtattcact ggcacaggca ttccatcgct cagtttcacc   12840
tgggtttgct gattaattgg aatgctgctg accgcaaacc gtgccaggcc cagtgtcggt   12900
ccgctcatcg tctgtggcat tggcgcgccg gcttctattt tctcaagttc agctgtaaca   12960
tttttcagtt cttttagcaat aacgtgaatt tttttacag cctgggttaa ttcatgagta   13020
gaggctttat caacccacct ctcaacctct cctccacagg ttcccattg tgagaaccgg   13080
```

```
gctacaccga cctgaatatt tgttaacgtt gtaacataat cattaagttg tttagcctct   13140
ggaattttat ttaaattctg taaattcgtc attaatgaac gcagcgggcc gttacctgaa   13200
gccatctcct ggaagttttc tcgcaggcta tttccatcca tttgttccag ttgcggtaat   13260 gttctttttaa gtcccttag cgcgatatcg agtaaaggtt gcttactttc tgctccaaca   13320
tcgttatttt tttctgccac ttttgtatcg ccgcctttta tgactaaagc ggcattcctg   13380
acaccaacat tatccttgct cttaataagg tttataaacc cttcgtcagc agcttttaca   13440
cactccgtga tctgcactgc taaacgttgg gtaaggggtt tgttcatatt tatacgggac   13500
attaacagtg cgtcattaac cgctgttccc ccatattttt ccgttagtgc atggagaaat   13560
gtctgtaaaa tcttttggtc ctgtactctg atattttccg tatgttttg caccacttca   13620 gtgttttta ataacggcat ttttccaagc caggttaata cttttgacga aaattttca   13680 ggcgcaacat atgccttatc agtattttcc ttagcaatat aaagtcgggc atcattcgac   13740
acaccaactt tgaaaacga agacaacgtt aaattattca atttctctc ctcatacttt   13800 agcatattcc tgcagtatgt ttttgagcgc ttcctgctga ttcacaaatg actcaagctg   13860
cgatataata tggtaagtat ttgtcagatc ggtaattgca tgtataagca acaacgtctc   13920
tgcggcatca atatacgcta acgtaccttc attattcgca gccagttcac cattaatcac   13980
cataatctgc cgccagatag aatcgccaca acaggcgat aacggtataa tcataccgtt   14040
caataaccag atatcatctt tagcttcaat agacgtaaaa atatcgctat cgagtaataa   14100
taagcactga ttgttgtcgt caaaagtgag cggtaaaccc aatttctcac caatattagc   14160
gataatatcc tggtgtgctt gcaatttact ttcctcttga attatatctt ttataagatt   14220
gcttcttcaa atttaatctg gttacacaat gtcttgatac ttttcgcgc ccatcgccgg   14280 gcgcaatatt tctctccttt aatccagtag aatagccatt cactacgcat cggaacacat   14340
atcagcagct ccttcggatc atttcaaca tgacgtaact tgccttaat aacaaaacgc   14400 gaactgtcag caatatcatc atatattgca gccatacctg aaccgggtac tacatgtgtg   14460
atgattttca taacaattaa tcttattcaa ttgttgtcaa gcgagagaaa aatactacac   14520
cctggactca agactttttt taacaacacg gcatatatcc gcaaaggtcg tcatatcagg   14580
aagatcgttt tcattgcaac taatgtcaaa ctcctcacta agaccaaata caatatcaat   14640
taaatccaat gagtcagcgt aaagatcctc aaccagattg gtctgaccat tgatactatc   14700
aacatcaacg gcaatacagg aggtgatcac tttttgact cttgcttcaa tatccatatt   14760
catcgcatct ttcccggtta attaacgctg catgtgcaag ccatcaacgg tagtaataac   14820
ccgatccacg ccaggtttat tcaggtatga ctcgtaagcc gggccagctc gccagctacc   14880
gtctccgata aggccgtcca gcacattact taacacatag tcagtttccc cttttagcct   14940 ggtcagccccc gcctctctgg caaactgcag tgcaatctca gccagttttt cttttgtgg   15000 atgatgagta atgacctctt tgagagtctc cattttcgct ttcaattctg ggtgcttgtc   15060
aatatcgcta cattgcgctt tcaacgctgc actctttatc gtgtcattgg gtaatatttc   15120
cgcacgcaag ccgtcaaacg ctctgcgtac agggaacggt gtggaggtat ctggctccag   15180
ggctttacgt atcacaccca aaaacgtctc acgggcgtcg aaatgcattg aatgcatatt   15240
cgtaacgctc ggtactgttg agaggaaact attttgctta aacttcaaac cagaaaatgg   15300
gccagtctta tctgtctgac tattatcatt atcggtcgta ccggctttat tacctgtaat   15360
taccgtcgtg tctgattgta aggtatcggt tttaacattc tcgacgccag ccagttgact   15420
ggcaagcggc ttcacattca caatctctgc cgtctggctt tgctgtttat tatcatcaac   15480
```

```
gccgtgcacc gtggcctgta ccggcttgcc gataatgctc ttgctggtta cgccatcgac   15540
ttcatcaaaa gaggttgttt cacccatagt gcccttttct gacgtgacca cctttccatc   15600
tttactttcg gatgaagcgt tggtcacagc ctctgccgtc gcatgagccg tgacgtcaat   15660
tttacccgcg atgccatggt caattgcccc tgtgctggcg ctgtgtgccg tctccgtttg   15720
atgcatagtc gaatccacac gcgaatgact atgacttacg ttgctgctgt tagtcgaatg   15780
gtgtgactcg ccattgcgtt ggctgttatc aataaatgtt cggctattat caatcgtctt   15840
ccggctatta tcatggttgc tattatcgat atggcgctgg ctattatcga catggcttcg   15900
gctattgtta atatgcttac tgttatccac gctatggtta ctgctatcaa tattaatatt   15960
gatattaata cccgtaggtt ctgcttttt cccaccatca ggtactggtc cagccgcagg   16020
ctccggaatt ttagggtcag gcagtttatc tgcaggaatt tttgcaaaaa cattacgtag   16080 cagcagggt atcaacgttt gcatttcaag gtgccgggct tcccgtccta cgctggtacc   16140
ctgctcttgc gttaattttt ggtggcacat atcaagcgcc tcaaccgcct tcgccgccgc   16200
tttgtcaaca aggtgcgtaa gattgctgcg ggttaacgga tctaacgtac agccaaagtt   16260
atgttcaatg cagctggcaa tatagggcat cacctcctgc ataacaagat tcgtcgataa   16320
tttacttaat tcaccaccag tgttattttt gataatatct aacagctgct tttccaggtt   16380
ttccagcttc gcttccgctt tctttgtttc tggcagccat ggcccaaaag ctgacttttc   16440
tttcaggcca tcttttatga tttgctcggt atactctgcc cccaccttca tcagtagcgt   16500
cttcgcctca ggagaatcac tggtggcgtt gagcgctgaa cgaaagagcc cggcaaactc   16560
cattatcgct ttcttaccgg cgacattatt tgaattggta aaaacttctt ttaacgcctc   16620
agcgtctttc ccgcatttaa acaatgcatc cagactcgcc tgtttgatca gcgcgggaaa   16680
atcttccagt tgcgggcctt taatttcccc tgacagcgtc gttgtggcac tttctctgac   16740
tgcggaaaga ttcgccgcaa gattcgtggc ctgcgttttg atctcggtct gcatacctgg   16800
tattatgacg gggggctgag tccttacact tgtaaccatt attaatatcc tcttctgtta   16860
tccttgcagg aagctttgg cggttttccag gctgctactt atcgtactgc tcagcacttt   16920
taccaggttg tcgtacaatg aattggcatt gctatatttt tgcgtcagcg tctgtaatgt   16980
ggttttcata ttttcttcct gcgctttaaa acccgactgc caggcttgat atttggcgtt   17040
atccatttcg agttttgagt cttttcccgg cgcgcctaaa ccatcaatat cctgaaccat   17100 ttttgtaat ggcgtcagat caacggtgac gacataaccg gatccataag atttcaggca   17160
gctattcggt aaattcaatt cactgagcca ctgtctcgct tccgcttcag tggctacttt   17220
aacgccgctg cctgactgag ctggaaataa aacggtatta ctgtttattt gattatattt   17280
attgactaaa ctgtttaaat catttttgag tgaggtaaca tctagcttaa cggtattacc   17340
gtccttacct ggtaataacc agcctcccat tttggaaaga atatcactga aggcctgata   17400
aaaatcggta tagactgcga caacgttttc ataaacgccc agatagctgt cacctatcgc   17460
cgatatattt tgggaaacca tatcccaaat ctcagcatca gaaatggttg ttctcggctg   17520
cgccataggc gaagcgctaa ataaggccga cgtcggcgca gaaaacgcgc tccgcaggtt   17580
ctcattttgt tctgcggata atgacacgcc agacttcgcc agagcattca ggctgctggt   17640
caactgctgg cgcgccagcg tgcgctcgtc attattctct tcagagatcg gtggcgttga   17700
ctgcagcgtc tgctgtgcct gctggatttt agtagccgcc tgcgataatg aaatgatatc   17760
tgtaccgcga tgttctgtgg tagacggtac cacggcagtc tcgacgtgct cgctcgccga   17820
gggagtctgc ggccgttcgg caacgatccc cggatgagga gaagcggaat aattttgaat   17880
```

```
attaagcata atatccccag ttcgccatca ggagcgcgat taaatcacac ccatgatggc   17940
gtatagatga cctttcagat taagcgcgaa tattgcctgc gatagcagca agtgcggatg   18000
ctttcgactg gttaatgctc tccattgttt tcagcatttc ctgaatcagg ctggtcgatt   18060
tacgtgaact ttcacgggct tcgtccgatg cggtgctggc aacacggtta ttcacctggc   18120
taatttgctg ctcggaacgt tcctgagtag cggcgtactg cccggacgcc cctgcaatac   18180
caccgaccgt gaccgagttc ttcataatca gatcgcccgt catctgcatc ttgcgcgcat   18240
caattcgggt catatccatg gtattctgct caagacgaat atcggattcg acagactcaa   18300
gacgtttcga cagaatagcc tgatgttcag gggagatttg tttattactg tctttaatac   18360
ccagactttc cgtggcgctg gttccggcat tagatttaag cgtcgcatca ttaagatttt   18420
ttgtcgcatc ggtaccggtt ttcttcatat ttaacgattt cagagaatcg acgccttcag   18480
caccgagttt gacgctattc tgcccgttca gcacgttttt aatactgtgg ctttcagtgg   18540
tcagtttatc gatcttcgcg gcattatgtt taagcgcgcc tctttcattc tgcagcccct   18600
tatattccag tttggcgccc acgccagtga tccccaactg aagcgcgctc tgggaaatac   18660
taccggacaa cgcattcatc ccttcgcgca tcatggagct tgctgtcgtt ttagctgcat   18720
caaagctgac taatgacaac ttaccagaca gtttgctatc agcctggttc aacgtcagca   18780
ttaacgtatt cgcggcagcc aacagcgcaa cggcactgga agacattccg ctaatatcaa   18840
aaaactttcc gacttctgcc tgctgctcgc gtaactgggt ttgcacaacc tcattcgctt   18900
tagtcgtgac attatttgcc agagcattca aatcctgatt catgtcggta ttttgaatac   18960
tggcttttaa aaaggacgtg atcgttccgg gggtttgcgt taatacccct ggcgcaggcg   19020
cgctcagtgt aggactcaac cccaggtcac tgactttact gctgctaata ccaatactat   19080
tcagaatatc tttagcgcta acggattgcg aagctgtctg tgaactattc tcaacagaat   19140
gattatttaa ataagcggcg ggatttattc ccacattact aattaacata ttttctccc   19200
tttatttttgg cagtttttat gcgcgactct ggcgcagaat aaaacgcgaa gcatccgcat   19260
tttgctgtac cgcagaagac atggcttttt gcagttccgc cgttaccttc tggttttcac   19320
caaatatttc tacggattgt ttaagccact gctgaatctg atccatggca aaacgggcga   19380
gcataaaatc agcaagcgcc tcgctggcat ttttaataaa tacgccctcg caacaccac   19440
cggctgactg ggctgcggta ttcgtgactt ccatgcccaa cgccacttta tttagggtat   19500
tacctaccag ctctttactt aaggcattcg tttgcaggcc catcttgcta cctacattac   19560
ccagaccgct agtaatacgt tgcatcccct gggtaaagag tttgctgccg ttttgcgcca   19620
actgtttcag cacgttaggc accaacttct taatcgtttc gcccatcatt ttgctcagcg   19680
cgttaccag tttcgccgcc cgccttttcc cgacaactgc gaccaccaca atgaccgcca   19740
ccatggcaat agcggcgaca atcgcaccaa caatgctgcc ggccatctct gccgttttct   19800
tatcgatgcc taatccttcc agcgctttgg taatcgcctt gccaatcagc tccattaacg   19860
gcttcagcac atgctccata atcgggttta gcgcctgctg aataaacgac accccgtcg   19920
ccgccttcac aatttcatcg gccaccatta ccgcaagtcc caccgcagcc agcgccagac   19980
tcgccccacc ggtaaaaaca gcggccacaa cgctgacaat ggttagcagc gcgccgagga   20040
ctttcccgat acatcccata atgcggttcg tttcctcggc tttgcgcgtc tcttcctgga   20100
attcagccga tttctttttcc atctccgcct gacgcccttc ctgcaaggcg ttgaaaagcg   20160
caagatcgtt ttgcaggctt tcttccgtat ttttgcccac aatctcaata aacatggcca   20220
tgagcatagt gaggcgggcg acatttgaca gattatcctg ctcaccctgg gaaacctgat   20280
```

```
tctgagaggc ggcattagcc gttccctgga atttggtcag aatgttatcc gctttctcgg   20340
ctttcgcttt ggcgtctgtg cctgctttaa ccgtcgcatc cgtggcctta tctaaggcct   20400
ctttcgcctc tgtcgcttct tttccggcct gttctaccgc ggcttcagct tgtgcatagc   20460
cggggtcagc cgggtccagc gattgcaatt tattttgcgc ctgcgtcagt tttttggtcg   20520
cagcgtcata aacactcttg gcggtatccg tcttttttgat actggcttca tagagatccg   20580
tcgcctcctg agcctctccc agagccgtct ggaattcttt cgatacctga atccccatct   20640
cttttttgtga ctcaatcatc gcctgccata ccgccagacg agactccagt tgagacagcg   20700
aaacatcacc cagtagcgtc attaacttgc caagcagtaa tgtcaattgc ccttcgctgg   20760
agagttttc ccgggcggcg tccgtaggcg gcttcagacc caccgtatta atagcgctct   20820
cgccggactt tgttccggct ttaaggtcgc ccgctttcgt tgccaccaca tctttaaaag   20880
ctttatccgc cgcttttaaa aagtccgtgt tcttacgaac gccttcaaaa gccgcctcag   20940
cgaggcgcgg attttgggta tatccgctac ggctaatgct acttgcgtca tttaccataa   21000
ttattccttt tcttgttcac tgtgctgctc tgtctccgcc gtttttagcg cctccagata   21060
gaccaacgct tttgcccgca gagactcatc ttcagtacgt tcattgacaa gttcaaaaca   21120
ctgtctggct tttgctgcct tacgcattaa taattgacac tgcccggtaa aaaaaacggg   21180
gcgataatca ttttttaagta acgtaaacgc tactgcataa aggtcacatg ctttctgaaa   21240
ttgttttttc agttggcata ccgccgccag tcccatggtg taatcgggat tgtaaaaatc   21300
ataaatgcat aagaaacgaa agaatgtctc agcttcatcc agtcgtccct ggttataaaa   21360
ctcataagca tgagcatata aaccgtccat catatcttga gggatcccat gaacgtcttt   21420
tagcgtggcg ccttcactaa cggcatccca aatcatttcc gcaacacgtt cttcgctgac   21480
attattttga taatccatta cttactcctg ttatctgtca ccgactttgt agaacttaac   21540
gactgcgttt atctgatgca gttattaaac cccgacggtg gttagtgaac attcaaaaaa   21600
cgcccaatga atacatcgct actgctttac gcggctcaat gccgtacctc gttttcttgt   21660
ggctgaataa cgtctttgcc cgcgttttct acctcttcca gccaaaccag aagacgtaaa   21720
acttcatcaa tttcttccag actcaccaga tcataacggc gatgggtttt gaaaagactg   21780
cgcgccagtt tgatatcgac gatcacaggt acgccaacct tctccgcata ggcgcggacg   21840
gccagtgcgc gctgattcgt ttcatacacc gagatcatcg gaatcggcat caattcgggt   21900
ttaaaataaa tcccgatcgt aatatgcgtg gggttggcaa caatcaggcg tgagtttttca   21960
atatcagatt tcacctgttc agacagaatt tccatatgaa cttcacgtct tttagattta   22020
acctctgggt tcccttcctg ctccttcatt tcacgcttca cttcttcctt atccattttc   22080
atatctttca tggtcaggaa atattccgca atagcatcca ataataagac aatcaatgcg   22140
caagcaaggc aagttaatac caatgcgagg agaagttcac gccaaatgac ggcaatacct   22200
acaatattgc catttagctg agaaaagatt tcaaccttat atttcttcca gcaaatgatg   22260
gcggccacca caaaggatga gagatacagt agggttttga ccgtatcttt aaccgtgcgc   22320
atactaaaaa gttttttttgc cccttctacc gggtttaacg ccgataaatt aggctttaat   22380
gcttctgtcg ccagcacaaa accggcctgt aataacgccg gtaatgcgga acacactaag   22440
cagagcagca taaatggaat cagatatttt aaccctatcc caaaaacggc caaactgtag   22500
tcagccatgc tctgatcaaa attatccgca ataatgatct taattatccc cataaactca   22560
ttaaatgagc catacgacac cagataggca attcctccca gcgtcaggca ggcgataatg   22620
agatctttac ttttaaatga ctggcctttt ttagcggagt cttccagccg ttttttagtc   22680
```

```
ggttttcctg ttttattcga ggacatgcgt cgcccctcgc tcgtaaaacc aactgcttaa  22740
ccctgtggcc tggaaagaga gtcgcagtac attgtccggt agtaccggag agaaataaag  22800
cagcataatt aaaacggcaa taccgctttt taccgtcagt gaaatcgcaa agcgttcat   22860 ttgcggagca aagcgcgaca ataaacccag gaatacttct gacagcaaca gcactaatac  22920
caccggactg ccagaaccaa aggcgttttg agccacctga ttaataaacg ttaatagcgg  22980
cggtaatgaa ggcgtgcact cgttcatcgg atcgcatagc tgatagcttt tatttaacac  23040
gtcaaccatc gtgaccagac cgccgttttg taaataaacg acagcggcaa acatattcag  23100
gaaattagcc atttccgagg tatcaatacc gtttgccgga tcgatactgc tacttagcgt  23160
tgcccctcgc tggttatcga taatacaacc cagcgcatgc ataacccaaa aaggccatga  23220
tagcagacag cccagcatga cgcctaccgc cgcttcttgc agaactaacg ggatcatcgc  23280
caccgataaa aacggcggcg cctcgttcaa tgcatgcggc catactccca atgccaccag  23340
gatgataatg gcgtttctcg gcgcgccgct taatacccg ctattcaaaa acggcaggaa  23400
gaaaaaaatc ggcgctacgc gagcaaaccc tagtgccgca gacgcaacca ggtgatgaat  23460
ttcaaagtac aacgcgtaaa gcattttta ccccttagcc aacgccagga atatcacctg  23520
acgcccgtaa gagagtaaaa cttcgccata ccagccagac agtaaaaaca agcataaaca  23580
cacgccaagt aatttaatgc caaaaggcag cgtctgttcc tgtaattgcg ttaccgtctg  23640
gaataaccct accaggaggc cgataatcgt tgcgacaatc gtcggccacc ctgacaggat  23700
caaaacaaga tagagcgcct tattacctgc aaacactaaa tcatccattt aactatcccg  23760
tctcgtaatg atgtcatgtt gcaatgtcca tatactgtaa tatcaatccc ttagacagta  23820
aggtccagcc atcaagcgcg acaaaaagca ccaacttaat aggtgtagat atcgtcaccg  23880
gactcatcat catcatcccc agcgccagta gcacgctgga taccaccagg tcgacgacaa  23940
caaagggcaa atagagataa aaaccaattt taaacgcgct ttttatttcg ctcagcgcat  24000
aagcaggtaa taacgcaaat attgatggtt tttcaattc atctttgtca cgctttaccg  24060
tctcggtctc ttctccatac tgacgcttca gttgcgcgtt ttcaaaaaac tgaactaact  24120
cgcgatctga atatttgatc agataatcgc gataaccatc cagaccttca tcaacgtgtt  24180
tacttaatga cgaaatatca ttaaaggtga catcttcgtc ctcaaaatag acgtaggcat  24240
catgcattat tggccacata acaaacatag aaagcagcaa tgcgacgccg ttaagcgtca  24300
tatttgaagg tatctgctgc aatcccaggg cgttacgcac catgacaaat acaatagaaa  24360
atttaacgaa acaggttcct gacgcaataa taaatggcaa caggtggaa atgccagta   24420 aggcaattaa tgagatatca ttccccatta ccagactcgc tcagccattc atggatctca  24480
acgcctaagg tgtcattcat ctgtaccagt tcgccattac ccagcaaaac accattcgcc  24540
ataatttcaa cgttaagttc agcattggtc ggcagtgata atagctgttg ctgccccatg  24600
gcttcgagtt cggcgagggt aacgttctta cgatacaaaa caaattccag tttgacgggc  24660
aattgattca agccaggcag agtttctgca gtttcagttg tattatttc ttcttcgata  24720 tgttgaatat ctaacgtttc cacaataatt ccccttcaa cacggttgaa atgacctaac  24780
tttttcgcgt agcaataaac ttccgcacgg gaagtacgaa tcaggagtac atctccgatc  24840
ccgattcggc ccagcaacga acgctgcgta tcactgctac cgattacaaa gcgcaacggc  24900
caacgcagca ttttcggcct gccgccccg actgcaggca gttcaggaag atattcaaac  24960
cacaggccgc cccgatcgct cataatgtgc aacaatttcc cttccggcag cgcgcttccc  25020
ggcacggggt tctctacgca taaacgccga caggacaaat gcggcacggg caactcaaac  25080
```

```
ggtcgctctg tcgcagcaag ccagggaacg accaggtgct cagcgccagc agaaaccgcc    25140
gcccccgcca gagcgggaga gacatgctca agccagtccc caggttgaat ccacgccgac    25200
caccgttttt ctgcatcgct caaccgaacc cacattcctt gtcgcgtcgg atattccagc    25260
gtagcttcct ggccatggcg ctggcattct gtcgcggttt gcgccaatag ccattcgcga    25320
cgatcaatct gtctcacacg caatgacatc aggcgtcatc ctcctcgcca gattgctgtc    25380
tgtgctgttg ctgctgcgga ttttgttgat cgtctcgcgt caggtgccag cgctggggat    25440
taccgttttg ccattgatca tgcaaacgat gttcaacctg cgtatttgac ggtattaacg    25500
aaaactcccc tgcttgccgc gcctgaatat tgacggaata gtcatttccc cagcgctgaa    25560
aacggtaagt cagcgagcta tcctctcctt tcacgccatc ggcagtcgga aaaatagtca    25620
tcatcggctt tgattgcgcc gctaaaggca ttttttcatc gccgccggtt aattggctaa    25680
gatcggcgat agtggttggt tgcagcggaa gctgagaaac atctttaacc ttttatgat    25740 ctttatcgtc aggcttaccg gtattggctg cggccattcg ggcaggtgcg catcccgcg    25800 ccagcggcgc gccctcttta cgaacgcctt cgcccgcgat ggctttatta tccccaggca    25860
atgccttgat attatcgtca gagattcccg tggcgttatc ggctacttca ctaacggact    25920
ccacggcttt taaatcagca gataattttt taccgcttac gctttctaac ggcctatttt    25980
tagacgatag caacgctgcg gatttatcta ctttggcctc cgcagaaatc aaaccgacag    26040 attttcagc agtgactttc aacagttttt cagcaatcct gagttcgcct tttccgttat    26100
gatgcagacc agaaacgttg ccattgtgat gttctgattt cgctggcgcg ccatgtcgcc    26160
atgccgccag taataccggt aaagccgttt ctttatgcat tacgaaagca tcgccatagt    26220
cgcgatcttt tttatcaccg gaatattctg tcttatgttt ttccaccgct ttttttaatg    26280
cttctgataa accgccaacc tcatcctgct gcggcagtaa aatgttcccg gatgaactga    26340
cagctgacac atcgcccatt aaattatctc ctctgactcg gcctcttcct gctgtatctc    26400
tcgctggata tagaatcttt tctgacggat tatccagcgt tgatagttcc cttctttgcg    26460
caaccaatat ttactttttt tctgaaactc ttccctttc ttttccagct cgctccgttt    26520
ttcctgaatt tgtataatct ggagttctaa atcttttatc tgccggcgaa caatagactg    26580
cttacgtaat aacgtataaa tttcctcacg actgagctgt ctgttttctg cacgcagcgt    26640
atctaataac aatttcagac ccgctatttg ttcaaggatc gcctcctcct cggcctgcag    26700
cccgcggtcc tcatcctgat agcgaagtaa tatcgactca cactgtgaat gaaataccgt    26760
acagcgccgc tgcaatactt taattctggt cagcgaatgc attcataccg ctcaacgtgt    26820
catcaaagga tgaatactgc gctaccggct ggcataacca ggctttcagg ctatcccgca    26880
tctgcatcgc ccgatcgtta tcgatatttt cgccaggacg atattctccc aagtcaatga    26940
aaagctggag ctcttccaaa cgcgtcatta atttacgcac ggcagatgcc tgttcagcat    27000
gtgtcggcgt cgtgacttgt ccaaaaacgc ggcttacgtt tttcagtaca tcgattgccg    27060
ggtaatgtcc ctgcccggcc agctttctgc tcagatacag gtgaccgtca aggatagagc    27120
gaatttcatc cgccatcggg tccgcctctt cctcgctttc cagcagtacc gtataaaagg    27180
cagtaatgct tccctcgctg gtcgcccctg ggcgttccag caagcggggc aaattatcga    27240
atacggaggc gggataacct cgacgggccg gacgctctcc cgacgccagt gccacgtctc    27300
gcaaagcacg cgcataacgg gtcatggaat cgataaaaag cacgacccgt tttccctggt    27360
cgcgaaaata ttccgctacg gttgtcgcca gttgcgccgc attgcagcga tcgaccgagg    27420
ggaaatcgga agtggcaaaa accagcacgc attttttcttt cttatgcgaa gcgcgcaaca    27480
```

```
tatccacgaa ttcagtgacc tcacggcctc gttcaccgat aagaccgata acaaagacat   27540
ccgcctccgt ttgctcgatc agcatatgca tcagcatggt cttaccgcat cctgcggagg   27600
caaaaatgcc cattcgctgg cctacgccac aggtcaataa cccgtcaatc gcgcgcacac   27660
cggtaatcag cggttcacgg acgccaacgc gtgaagcgta agacggcggt gcgacatcaa   27720
taacgcgttc ttcgctaatc ggcgccactt caggggtaaa acgctcaacg attttccctg   27780
tcggatccaa caccgcgcct aataccgagt atcccaccca cgccgataac gcacgtccag   27840
tgggataaag cacgacatcg cggctcagcc cctgggcatt gccgataagg ctcagcacgg   27900
tgcgttcccg ctgtaagcca accacctgcg cacgtgcaac aacctgtttt tggtgccagc   27960
cacggcgtat ttcacacagt tcgccaatgg ccacatcgcg caattccgcc tcaataattg   28020
ggccggttat tttttgtggg taggccagat attgcagtaa acgaggtgtt ttcatctcat   28080
tagcgaccga ctaaaaactt ccagatagtt gtaaaaccca ttcaaggcag tagagaactt   28140
ttcaccgtca gataaaaaat ccggatgcac taaggcttta agcattagct ccccattctg   28200
ctcccccagt agtaattgcc cgccgcgggc aaaatggcat ccttccatga tggtcattaa   28260
gatttcataa gcccgctgtt gtaataccac catgctgtca gcacccaatt gcgcccagat   28320
ccatacatca tcgtccttga cgctgataca gatacttggc aatgcaaata aatccagaac   28380
aattgttgaa tggctatcta ttcctccgat gagtgaagga tcgcaaccac ttacttccag   28440
tgcggaacga actaattcag cgatatccaa atgttgcata gatcttttcc ttaattaagc   28500
ccttatattg tttttataac attcactgac ttgctatctg ctatctcacc gaaagataaa   28560
acctccagat ccggaaaacg accttcaatc attttcttaa taaatcgacg gacatcgaca   28620
gacgtaagga ggacaagatc tttatgtgca atcaataaat catccaactt aagtgtaatg   28680
agatccatca aattagcgga ggcttccggg tcaaggctga ggaaggtact gccagaggtc   28740
tgacggatcc ctttgcgaat aacatcctca acttcagcag ataccattac tgctcgtaat   28800
tcgccgccat tggcgaattt atgacaaata taacgcgcca ttgctccacg aatatgctct   28860
acaaggttaa tgacatcttt ttctcttggc gcccacaatg cgagcgcttc cataattaat   28920
ttcatattac gcacggaaac acgttcgctt aataaacgct gcaaaacttc agatatacgt   28980
tgtaccgtgg catgtctgag cacttcttta agtaaatcag gaaatttcgc ttccagttgg   29040
tccagcatat gttttgtttc ctgaataccg aaatattcat tgacgttgcg cgccagcgtc   29100
accgccagac agtggtaaag ctcatcaagc gcgttccgca acacatagcc aagctcccgg   29160
agtttctccc cctcttcatg cgttacccag aaatactgac tgctaccttg ctgatggatt   29220
gttggattaa taccaaagga cacgacttca tcggaataat ttaccactcg catcaaatca   29280
aaatagaccg taaattgttc aacacggatc tcattaatca acaatacgat gctgttatcg   29340
tccaggccct cgccatcgcg taacaatact tccggcaggc gcacgccata atcaataaag   29400
aactgactac gtagacgctc cgcaagttga gcttttttcca gatcttcacg ccggctcttc   29460
ggcacaagta atatcaacgg tacggtctct gtagagactt tatcgagatc gccaatcagt   29520
cccaacgacg cccccttcttt ttcctcaata ctaagcggct gctcgccttt gctggtttta   29580
ggtttggcgg cgctacgttt tgcttcacgg aatttaaaat agaagagtac gcttaaaacc   29640
accgataaaa taacaaatac cggcagcggg aatcccggca gagttccat tgaaatggtc   29700 aaaatagccg taacaaccaa tacaaatggg ttgttcaaca gctgcgtcat gatattccgc   29760
cccatattat cgctatcgcc atttacgcga gtcacgataa aaccggcact aatcgcaatc   29820
aacaatgcgg ggatctgggc gacaagacca tcaccaatgg tcagcatggt ataagtagac   29880
```

```
agagcggagg acaaatccat accatggcgg gtcatcccca ccgaaatacc gccaataaag     29940
ttcacaaaga taataatgat gccggcaata gcgtcacctt tgataaactt catcgcaccg     30000
tcaaaggaac cgtaaagctg gctttcccct tccagtacgc ttcgccgttc gcgcgcagca     30060
tccgcatcaa taataccggc cttcaaatcg gcatcaatac tcatctgttt accgggcata     30120
ccatccagag aaaatcgggc cgcgacttcc gcgacgcgtt ctgaacccttt ggtaataacg    30180 ataaactgga ccacggtgac aatagagaag acaacaaaac ccaccgccag gctatcgcca     30240
ataacgaatt gcccgaacgt ggcgataatt tcaccggcat cggcttcaat caagataaga     30300
cggctggtac tgatcgataa tgccagacga aagagcgtgg taattaacag taccgcagga     30360
aacgttgaaa aactgaggat tctgtcaatg tagaacgacc ccataaacac caatatcgcc     30420
agtacgatat tcagtgcgat caggaaatca accagatagg taggtaatgg aatgacgaac     30480
atagaaatga tcatcaccat tagtaccaga atcagtaatt caggtcgtaa acgagcactg     30540
ttaagtagag aaagcagcac tataggtatc ctgttaatat taaattaaga cagctttttca    30600 atagtacgac gctgttctgc catttcatgc ttgtaggcaa tatcggtcat actacgtaac     30660
gccattaaca attcttcctg ccaatattct tcataaaaga gtgaagaggg tatggcttta     30720
catacttgat aaaatatctg caaaaaggat gcatgttctt tatgactaag caataacgca     30780
ttcaaaccta taatatcggc taacagcgaa tccacttcat gtggctgttg caatagcgaa     30840
agcatcagta gtagccacga cgactcctcc gcattaaacg ctttggtaaa cgaatacgac     30900
aacaatgtac tcacaaacag taggtcagcg gagcgcaaca ttttaagttg cgtcaggcgt     30960
cgtaaaagct ggccaaactc caggcgcgaa caactggcgt cattcgcgtc aatatcggtt     31020
aatagcgaac cctcaataaa atccagtacc accagtcgac gttgatagcc ataactggct     31080
atccagtcag agtaaatctc cacttcatgt gattcactct ggataaattg ccgatagctg     31140
gcgcgcaata agcctggttt taacgataat gttttcccaa aaagccgggc cttcaacgca     31200
caattaatcc ctgccttgag ggtcttcgga tcggtttgct cttcaacgtg cttaagtaac     31260
gactccagct ttttccgcac gatctcttcc aggtctttac gacgaagcaa ttcgcgtaac     31320
acaaggacta aatcactggg gtcaggaaat aagctacgcg cctgacgtaa aaaatcttct     31380
aacgcgccgc catgtacgct aattagcttt aagatttgct tcgccttcgg taaagcctca     31440
tcttccagca cgcgttcaaa actgttagat aaaattactgg attttttttc ataatcgcga    31500
cggttacgaa attgcgccag cgccgctgac atttcgtccg tcgactggac aaatttttgt     31560
acttccgccc ctgagacga atcctctgcg gcctgttgta tttccgcctg ttgcgcatca     31620
gtatgctggg tcgcatcctg atgagatgtc tgccgggaca atattctgga aaatgaaata     31680
ccggaggttg agccaggaat catttaattg cctcctgacc tctatccaga taaacacgaa     31740
cccatttctg taacttatcg tccccactcc aggcaccgct ttgcttcaga atattgttta     31800
ccgattcgct ggcatccggc gttaacgggt cgacaatttc ttttggttca atcatgaaca     31860
cacgaacaac attactttta ttcttactgg aatagcggaa caggctacca ataagcggta     31920
atttgcctaa aaacggaata ctttggacag tatcggtatt tgcatcccgt gtataaccac     31980
cgaccagcaa acttttttccg tgcggcactc tcgcaatagt gctaattaac gttcgcccga    32040
cttcgggtaa cgcatctacg gaggtggtag tatcggattg cggcgtctta tcgttgccat     32100
cttcaatgtc cagcgacatt tctatctgac catctgcgga aaaacggggc agcactcgga     32160
tcattgttcc gtatgttaca tgctcaagcg ccacattacg ttccccaatc agcttggtgt     32220
aaaacgttct gttgttatca aaaatagcgg gaacattttc ctgggtcagt aataccgggc     32280
```

```
gtgaaaccac cgtcgcctgt ttcttctctt ctaacgcatt gaccgcggcg atgaatcgac   32340
tgccatcgag ggtacttatt gaagactggt ttaatgacac gccaagtttg tccccaatag   32400
taatgctgcc gctccatgaa gtgcccaaac gctccagatc gcttttatta agatcgacaa   32460
tccacaggga taattctacg tgacgtttgg cgacatccag cgctttaacc agcatttcga   32520
taaaattcac ctgctcagcc gttcccttta ctaacaaact gttggtatcc ggataggcca   32580
cgattttaat attgcccgcc gcggcatttt gctttaaagc ttcctgcaga ctcatgccac   32640
cggcataatt tgctgcttta ccttttttctc cattcgctga aaacgctggc atcgccgggg   32700
gttcgctact gacaatatta cctaaaggtt gctcttctcc ctgcaacaac ctttcaatgg   32760
ccgtggcaat accggggata accatttttct gatcgcgcag attataggta cgatcgccca   32820
cgaaggtatt gttcagacgc atcacccctta ttttctgacg tcccagctca ataccatcgt   32880
tttgcttgtc catcatggtg gcggcgttga ccaccatatc aacatagacg ggtggccctg   32940
aaacatagaa tgttcccttta cggttatcgc cacgtagcgg gtaattttttg ttatataaac   33000 ctgagcgttt tagaaaattg ttgaactcat tgagtgagac gttgcgtaaa gaaaccacgg   33060
cattgcgcat ttcactggcg tcataaatat agatagcctg cccatcgaaa taccaaatca   33120
gccccagttg tagggaaagc ttctccagta atgcgttagg atcgtgaaac tcaaagttgc   33180
ccgtaatttt ttttcgtgcc gccatttttgc taacaatgac aggctccttt agctgtagcg   33240
ccatggcatc gaaaaatgtc cgcaggctat cgtctttcgc aacaaaccca cttcccgtta   33300
caggtatttt ttcactagaa taaccaggtg taaccagaac aagcgcggca catgccagca   33360
ctctggccaa agaatatgt gtcttcattt gtctgccaat tgaataatat ttgataattt   33420
ccgcggcgaa acgccgatca gctctttgat ctcactagaa aaatgtgaag gcgatgagta   33480
accatgatta acggctaatt gggtgatgtt ctcgtggcct tctacactat tcagcagcga   33540
ttgcgccata cgccagtttc gtaattcact cttcgctttt ccgcccaacg ctctgctgca   33600
caaacgacga aaatgggtat aagaaacgcc atagtcttct cccagcattc tcatcgtgtt   33660
gccgctggtt gactgagcga gtaaatagcc aaccaaccag taactctcgc ttttttcgtaa   33720 cagagccagt accttattga aggccggaga aggtgtaata atttgctgca aaaaccagta   33780
ctcgcagcgt ttacgatctt gccaaatagc gcgaaactca ggactcagca aaacccattt   33840
atcggattca gcatatgtcg tgtccactaa tcctgcgcca tcgataaatg ccagtaattt   33900
gctgagtact tcaattttta acggtcgaaa aaccaggtct cctgatactg gtgcgacaac   33960
ggcctgctcg caaaaaagca gcgcgccttc ctgaatcagg caattttcat tgtgtcggct   34020
ttcagaaaat gacatatgca gcttttgcgc ggaacacgtc tgtataaacc atgcttccgg   34080
gctgcggatt ttccgcttct ctccttcttt aagtacttcc tgcgtattta gcatagttgt   34140
cagcaccagt taaaaatcat tttaatatgt aaacaatacc gggagcgggt ggcaaaatcc   34200
tgatgcaatc attatgaaac tgatgccgcc cgctaattaa attggccaac ttgcacagtg   34260
cttgctgatt taaaatagaa aattagctca tagtgtataa attctggctt attgttctgc   34320
agcagcaaaa attcagatat tgtcatctgg atggagaatt aattatttat tcaggagtt   34380 ttttttgcta gcattcctga aacgcattcg cctcttatca ctattgtcag ataacattct   34440
gacggttgtg taaaaacatt gcgcctcatt ctttctgtagt tggagttaat atgaaaaaat   34500
tttatagctg tcttcctgtc tttttactga tcggctgtgc ccaggtgccc ctcccttcct   34560
ccgtgagcaa accggtacag caacctggcg ctcagaaaga gcaactggcc aacgcaaata   34620
gtattgatga gtgtcagtct cttccgtatg tgccgtcaga ccttgcgaag aataaatcat   34680
```

```
tatcaaacca gaacgctgat aattccgcat caaaaaatag cgcaatcagc tcaagcattt    34740
tttgcgaaaa atataaacaa accaaagagc aggcgctcac cttcttccag gaacatccac    34800
aatacatgcg ttcgaaagag gatgaagagc aactcatgac cgaatttaaa aaagttcttc    34860
ttgaacccgg aagtaagaat ttaagcatat atcagacgtt acttgctgcc catgaaagac    34920
ttcaagcctt ataa                                                     34934
```

<210> SEQ ID NO 2
<211> LENGTH: 25262
<212> TYPE: DNA
<213> ORGANISM: Artificial Sequence
<220> FEATURE:
<223> OTHER INFORMATION: Salmonella pathogenicity island-2

<400> SEQUENCE: 2

```
ttatggtgtt tcggtagaat gcgcataatc tatcttcatc accatacgta acaaggctgc      60
aacgggttca ataacgtttt caggaatttt atctccgcgt tccacttcaa aaataatga     120 gcgggccagc tcaacatttt caacaacggg gatgcagttg cgttcagcga tgttaacaat    180
atagttagct tgagcatcac tgcctttttc caggacgcgt ggtattggca tatcggtggg    240
atgatagcca agacaaaccg caatatgcgt tggattacgc actaccgcaa cagattgttt    300
aacagattga gctaaactcc cactttgtat ttcactctgc atttcccgac gccgtgtctt    360
catttgagga tcgccctcca gatctttatg ctcctgtttt acgtcatctt tactcatttt    420
tagatctttt ctaatcttat aatattgaaa agaatagtcc agtatgccaa cgacgatata    480
aaaagccatc accccaaccc ataaccattt tattaaagaa gaaaccacaa gcaggccaca    540
ggctaaccca cagtacggta gcgcccgaaa agtactggca taataataaa agaaaaaagc    600
aaagataaga gatagcatga taactttcag gctggattta cataattcta ctacgctatg    660
taaagagaat atctgcttaa aattacttac cggatttata tgctcgcttt taaaacctat    720
ggccttgctg gcaataacca ccccacctg aagaaacacg ctaccacag tagcaactat     780 taccccagcg cccagaaaca gcagtgcaga agtcagtgac tctattaaag catgactcaa    840
ttgcgttaat gcataagaaa atggtttatt tactaattgt aatgtgaaag ttattgactc    900
aatcagtatc aaaatcatct tttcagtaaa gaaatgaaaa tacaaataaa gcgcaatcag    960
ctgaaataat gatgttattt caatacttt gacaacctgc ccttccttac ggccatcacg    1020
taatttcttt tctgtaggct gttctgtttt ctcgctcata cagatggaaa ccagtctttt    1080
agataaatat aaaatttatc gctttcaacc aaatagtgat gaagagcata agggaatgag    1140
atcaggagcg tcagtagaac cgatatactt ttgagcggca ttgagaggaa aaacacattc    1200
aattgttgtg ccgaccgatt taaagacct aaagccagat cggctaatac catacatatt    1260
atggcaggaa gagagaagct gatacataat tgataaagcg ttctccactc tgcctggata    1320
tattttaaaa attgctggtc aaataataaa gtacgccctg gtgtaaata ttgatatgac     1380 tcatacagaa tgtttaatat aaactccatg ccgccgctta taagaaaat aacacacaag     1440 aactggctga aaagcaagcc aaaagtgag gtttcagctt ctattgtaga attgaatatc     1500
gtacccattg tcgcgccacg taaagtatca agcagaaacc ccgccatatc aacggcccaa    1560
aagggaaccg ccgcacaaaa cccaattaaa aaaccaataa tcacctctcc ggtgactaac    1620
cctaaccagc tgtaatcttt accaatatgc atcataatct tctgctggta aatgattggt    1680
aatatgggaa aggtaagtga cataagcacg ccattacgta aaatcgcgga ccctaaactg    1740 ccactttta ataggggaag taataaagag aggctcaatg gtcgaataaa agccacagcc     1800
```

```
aatgcaataa gccactcatt tacctgttgt gccattcaac catgctctcc aactcgtaac    1860
attatctgcc gggtataatt caacaggata ccgctaagcc atgggtagct gaccattaag    1920
gttattgcaa ttgccaataa tttaatcatg aactgtagcg tttggtcctg tatttgagtc    1980
aaggcctgaa caaggcttac gatgacacca actaccgatg ccaccaacac caccggcata    2040
gacgtaaaaa ggacgatcca taaaagttgc gttacaaatt gcgtcaattc agaatcattc    2100
atgaaaagct ctgtaccaat tgcgccagtg tcagatccca accgcctgcc agtaaaaata    2160
ttagcagctt aaacggtaat gaaatggtca ttggcgatac catcatcatc cccatagcca    2220
gcagtatatt tgaaataagc aggtcaatag ccagaaaggg aagataaata agtaatccaa    2280
tccgaaatgc ctgcgtcaac tgactcaccg taaatgccgg aattaatatg agcaaagaat    2340
caggttttat ctttcttttt atgtcttcag gccaggttcg ttttatcaaa ctccgaaaat    2400
aattggcttc cttctcttca gagttttttt gcaaaaactg tcgataaggc gctaatgctt    2460
tactgtccca ctcagacgtc cagaaaggag cgccagcgac ctgaaccgga tgccagcgct    2520
cttttacagc taatagcgtc ggccccataa tgaataagga aagtacaagc gcgaggccat    2580
acagtgcgat atttggggga acttgttgaa tacccagagc atttcgtaaa atcgaaaata    2640
ccaccgccag tttaaggaaa gaggttccca tgacgataat gagaggcagt attgaaagca    2700
gaaacaatat accaatcagt tgcaaaggcg aatcgggtaa agacatactg tatctctcat    2760
gacacgacct agaacgctat tatattgttc gcatattatt tttcttatca ggtttacgct    2820 gtattttgc aaagataccaa acgtgtaata cgcaccataa attcattgcc acaggcaatc    2880
aactcacctt gcccaataat acggtcattt actcttatcg tcacctctgg cgcaaaacat    2940
ccacctacag gcaaaacgtc ccccgtttta agttgtcgta attgtccaat ttccagactc    3000
gcacgtccga tctcaaagag cacctgttgt ggtatctgct caagttctac tgaagatgtt    3060
ccgtcactct ttgacattgg actccctgac gcaagtagcg tttcgatatc ctggactaat    3120
tcatcaaatt tcatcgtgtt atcctctgtc agcaacaccc tcgcgtagat ccccccaggt    3180
agttgaatag caaaaaaacc gagtctgatg tcgccaaagc aatgaatccg aacgccatg     3240 ccgatttcga tagactcaag ttcaattaac gtaagctggc accagcctaa atatacaggg    3300
actactacag gaggggcagg ataaatctgt tgtcgcgcag cagaaagctc tccgactata    3360
ttgcgcaaaa aacccgttgg ccatgtaaaa ataatgctat ggaactcatg ttcttcaact    3420
gtccatttaa tatgcaacgc tagctgatgt ggtagattac tgcaggatgt tggcggttcg    3480
ttctgacaga gggttgcatc actggcttgc aataacggcg ccagccccca ttcagctatt    3540
ccatatagca attcaggatc gatagccgat cgattagcgg tgccaattaa cccttcacac    3600
cagcgctgcc agcattcttc tgcaatccac accctaccca gctcattatg ataatttatg    3660
gtaaataatg tcccttgctg tactggatat tgttgcatac tcaatgtcag ctcaccaatg    3720
gtagcgcctt gcgttggaag catctccatc cacggacgct cttcattcgc tattcttaac    3780
atagaatatc tccagggaaa ttatataccc catatgcagc aactgagact ccagccactg    3840
ctttagcgct ttcatcgaac ggtaaatttc atgatgaggg acattgattc ttaactgaat    3900 tagccccct gattcacaga cttcacactc tacaccgtca agataaccgc cactaacacg     3960
ataacgttgc gtaaaaacca cgttcttatt caatgctgca ggaggattat tctcaccaat    4020
gggtaatgcc tggtgcatga gttgttcaaa gtccatacgt tccgcctccg cctcgttatc    4080
atcctgataa gactggcatg gcaacccaag acttccctca actttggtaa tacgcatcgc    4140
ttaataccat agtaattttt tctttctttt tcataagcgc attaaaattc ttctgtaatt    4200
```

```
cgcttcgccg ggagacaagc tgctgatact gattctctaa ctgctgccgt tgcgtcaaaa    4260
agctctgcgc ctgagtgaat aacccggcca tttgttgttt cttatccaac aataaatgac    4320
aagataacgt accttgccag cccattaatt ctttcagtct ggtagacact gctaaagcgc    4380
gcgtctggca aatctgctgt tccgtaataa tcgcctgttg ctgctgatca agtacggtaa    4440
gcttgccgcg taattgcttt tcacgccgcg cgattatctc cagcaaagtt tccatgatca    4500
ctcggtgagt atttggtgta attttttctat aagtagctcg ggtccgcata cttcatcctt    4560
actttgtcgc aaaaatgtgc aaatatccgg ataggtatca atggctttgt cagtatcagt    4620
atcaactcct cgctggtatt ccccaatgcg tattaacagt tcaacctcct ggtaaagcgc    4680
caggcgccgc cgcaatatcg ccgccagttg acgatgctca tggctggtaa cgactggaaa    4740
aacgcggctg agcgttgcca gcacgtcaat ggcaggataa tgcccctct ctgcaagccg    4800 ccgggatagc acaatatgtc catcaagtag tgaacggact tcatccgcca acggctcatt    4860
catatcatcg ccttccacca gtaccgtata aaatgcggta atactgcctt tttcccccat    4920
tcctgtacgt tctaaaagtc gtggcaatgc actaaatacg cctggcggat attctccaga    4980
aactgcggtc tctccggcgg ccagagcgat ttctcgtgcg gccctggcat aacgcgtcag    5040
tgagtcggca agcaagacga ctcgctttcc attatcgcga aaaaattctg ctatcgtggt    5100
agccacaaac agcgccctca cgcgctctaa ggcgggtctg tcagaggttg cgacaacaat    5160
gacacagcgt tttcgggtct cttcagacag tgtaaaatcg atgaattcgc ggacttctcg    5220
tccacgttca ccaattaaca ccagaacatt gctgtctgcg tctggcgcat tacacagcat    5280
cgccagaagc gtgctttttcc ccacgccagg agcagaaaaa atacccactc gttgcccttc    5340
gccacaggtt gcaacgctat caatagcgcg aatccccgtc attaatggtt gagtgatagg    5400
ctgtcgaacc attgcgggag gaggcattgc atcatagtct ttccagcaga cgtcgggcag    5460
ttcgcggcca tcaaggggac gaccaaaaacc atcaatgact cgccctaata acgcttcgcc    5520
cacgggaacc tgatggcttc gccttaaggc catcacttgc tgcccgcagt gaagtccgat    5580
tgtactcgta aaaggagata gcaaagcttt gctgccatta atccccacga cttcagcaag    5640
ttcttctcca ggctttatac agcacaactc acccataaat accccaggca accacgcatt    5700
taacaacgtt gcgctgacat cctgaattcg gccccatcga caataaccat cgggggggcgg    5760 atatttcagc ctcagacgtt gcatcaattc attcttcatt gtccgccaac tcctcttcgc    5820
taaggtcaat actttctacc acttgtataa ggctctcctc tcctaattcc tgccatgaca    5880 aaaatcggtac gtcgaacaag gtggcttctg taattttttcg caagaaacgt cgggtgtcga    5940
cagaagtgac aatgaataat ttggctgact gcttcagcgc ctgctcgata agttgcagga    6000
tctgcgtctt atgacgagac gacagcgcag tataggtccc cattaccgtc tggcgaatgg    6060
attcacgcac gaggttctca ataccttcgc cgatccgcaa atcggcagc ggttttcctt    6120 ccggattaag acgacgcaga atatgacggc gaagcgcgat acggacatat tctgtcaaca    6180
tcaggacatc tttttcacgt ggcgcccagt caattaaggt gccgaaaata agacgtaaat    6240
ctctaataga aacccgttct gatacaagcc gttgcaaagt ttcagcgatt ttattaatgg    6300
gtaactggcg ttgaagctct ttcaccagct cagagtagtt ttttttccatc gcattcatta    6360 gataacgcgt ttcctgaaca ccaataaact ctcccatatg ccgaagcagg acacatttta    6420
ataaggcaga gatacgttgg ctgcccgcga aaacgtccag tccaaaacct tgcgccttat    6480
gggccatgtc ttttgtaagc caacagatct gccccatccc gttcggtaac gtctggctgt    6540
cacccaccac actagcgtcc gcgcctatca ataaataatc cgcctgagcg ggaatagata    6600
```

```
aactaaatac gggttcctga tatagcagta ccgtcaattt ttcggtgggt tcaggcaaaa   6660
cctcaatatt cacctcaggg agagggacgc cggtatcctc aaataaaaac catctcatgg   6720
cgtcaatatc acgaatcagg tcggcagaat gtaacgtcgg gctaagacgt aagattagag   6780
gacatgcgcc gggaaccata ctatcttttt ccggtgcttc gacgccattt gcggaaacca   6840
cagacttttt gcggcgaatg aggataattg gcaatgctaa caacgctgaa agaaagcga   6900
gagtgataaa aggaaagcca ggaattaaag cgaggagcat taaaaccaca gcggttaata   6960
tgagcgactg aggttgtctg gcaatttgag aactcaactc tgtcgccagg ttctggcgtt   7020
tctcaccccgg gacacgggtg acaataattc ccgcgctaag ggaaatcagc agcgatggaa   7080
tttgcccaca taaaccatct ccgattgaca gtacgctata agtgtgaaca gcctcactca   7140
tcgacatatc atattgtacg atagcgataa tgataccgcc gataatgttc accagaacaa   7200
caataatacc ggcaatcgta tcgccttaa caaatttcat cgcaccgtcc atcgcaccga   7260
gaaagcggct ttcctgctgg acatgctgtc ttaatgtacg ggcatggtct gcatcgataa   7320
ctccggcacg caaatcgcca tcgatactca tttgtttgcc tggcatccca tcaagcgaga   7380
aacgtgcgct aacttccgcc accctctcga tacctttgt aatgacaata aattgcacga   7440
tagtaatgat ggtaaatacg accaacccaa cggtgagatt tcctcctacg acaaacttac   7500
cgaaagcatc cacaatatta ccggcattat gttgtaacag taccagccgt gatgtgctga   7560
ttgtgagtga caaacgatat aatgtagtaa taagtaataa agacggaaat accgataaat   7620
cgagagggtc actaagataa atagcaatta agagcaggat cactgaaaac ataaggttga   7680
tagtaatcag gatatcaacc atccaggtcg gcaaaggtaa cagcatcatc acaatagcga   7740
ttaataacac cgtcgccaga accatatcct gccgacccgc gcatacactg agccactgtt   7800
gcgccctgac tccctcacct aaccatgaac gcattgcgac tccagaaatt ttatttgtcg   7860
atgatgtaat cgtaaccaga gctcggcgga gctggaaaga ggtggagaac aactcattgc   7920
aagcccatcg cgcaacaaaa ataatcgttg aggaatacc tggaacgctg cgggtttcca   7980
gttagccaac gctttaaaaa gcagttcttc gtctaagaag gtttgcttga gtatctgaca   8040
taagtgaata cgacagttat gatagtttag ataggtttca tattgtcctt gccgccagaa   8100
catattggtc gctaaaggcc gttcagctaa tcctgctaat tgaataaaaa gctgaatatt   8160
acgttcagta atgagatccc aatccatcct gacgcctcat gatgagccag aaagccaatt   8220
tacctaaata ttgaaagcca ggtatcagaa taaaacctga tttatcttta cttcacgaag   8280
cgtttcgaga atttgttcac gttgatcttc gtcgttaaaa cagttatcgg gtatcagcat   8340
aaactgcgca tcaagttgtt ggagtaaccg attgaacatc ttcgatgaag aaactatagc   8400
ggtaagtcta tcaagcaacc aatcactgaa aagccagcgc tcacaaataa tatcgagtag   8460
tagcggcagt aatgtattag gcggcaactg gcaaatccac tcctcacgct ggcactcttt   8520
ttcaaggcca aggaataaca gcaaacgacg caaacgtact aatgctgcgg ccaaacgact   8580
ttgctccgag ggttcgatgc atatgctaag ttcaaaggct attgctctta gcaaaatacg   8640
gacccgttca cagcgatccg gccagtctgc cacgcgtctg aaccactgcg ataagggcat   8700
ttcatcgttg tctatcgcct gttgcataaa acgcttcagc gaggacagcg tagcggtatc   8760
cacttcgcca agttccagta aactaaaaac ggcaagttcc catccctcct ccgctgtaag   8820
cgtatccagt tgcgattgca aatcgcgttt tttctttttt gacaacccgc cggcagtaag   8880
cgccattgca agagcgataa tttgatacgc attctgtaaa tcaggatcac tattctcttc   8940
ggtaagcgga cgcaacgctg ccccattatc ctcctgtatt tgttttatca aacgcagcaa   9000
```

```
agcctgctgc ctgcgctcca gtttctcagc atcagtgaat ttattacttt cgcgcagttt    9060
accactcagc gccattccta tttcttccat cgtctcatag agcgctgccc ccgtcgtttc    9120
ctgtaactcc tggagagcta acattgaagg cgaaataacc tcttgttcct ctataacctg    9180
gccaggggta aatgctgtag ggggcgtcat ttttatctca ttaattttaa tattcatcgc    9240
tacctctttt atcttcacca ttacgtaacc atttcagtaa cgcgttgaaa tgacgagaaa    9300
gtgaaaactc aacggcatat cgtgttgagg aaagttcagc ctgatcggga gagaaaccag    9360
gctcgataat caacgtaaac cgcttgccaa aagtttcacg catcaatgcc tcttttttcag   9420 gatgaatacg caaataaagc gctccctctt ccgccatagc cgtggcctgg cgtgccagac    9480
gatggcacat aacactgtct accgactgtt ggtcgaacca ggccaacaga acctgttcta    9540
tactattttt aatatgatgc gctgcgtgat cgaccaatga acgaaattga ttttcatctt    9600
cttgtaaatg ttttacatgc tgttccagcc attccacttc catttttttcc agcgtatttt   9660 tacgcaagca cgctagttct tgttgctgct caactttctg ttcacgctga taacgatagg    9720
cgtctcggat gattttttca gccttacggt aagcggagct cacaatagca tgtgaaactc    9780
tcttagcttg ttgctcttgc gcaaataaag ttaattgtaa tgttatccac tgtgactcaa    9840
taatatttcg agcgggtagc ttatggttaa tttccgtcag aggaagtgaa gtaaaactca    9900
tagcaaatgc tccatgaaga taatctcggt aagagaagtc ttcggccaaa gtatacgctg    9960 cggaggggt aataatacta atagcgcatg taaaaccgca tcgtcatgcg cttcccgatt    10020
aagaatggcg gtaccgatct gcaatgcagt ttgttgcatc acttgcggag gaagtatttt    10080
gccatctctt tgccccaacc aaccatatag ctgccagatc tcatcctcgc taaaccactg    10140
tagaagcaat tgccgatact ctggtagcat aaaaatagtca ctacacctga gtttgaataa    10200
tcccagccca aaggcaaatg ccgatatacg cggcgcaaga cgaacctgcc gcttttgcct    10260
gtcatttaaa caggctggaa taacagagct tcctcttagt ctatttaacg ctctgtcaag    10320
aagacgatcc aactcgggcc gatcgccata acgccagcag tttgaaagat gaaagcccag    10380
cttatccagc cattccggta cagcgtaacg agcaggttgc cagaaataac gataaagttg    10440
caacacctcg ggatcaggtc ggctcaaaaa cggcgtctca ggcaaaaata gccgatcagg    10500
atgcccactc ctaataacag tcctgtcaac gataacatca actgataagg gtatttcatc    10560
aaccacttca ccaccttccc tttattggcg ttgataacgt ccataatcca gaatgtttgt    10620
ctcgcgggta cgtcagctac cattctgaat tcagcaggct gcatcaagag actaatctta    10680
ctgtattgca acccagggat tgacatctct attaaatcct taattttttac ccgaaaggcc    10740 tccatattga cctgtggtga atattttata aatacggcaa ctgagctcgg agaagcgtta    10800
cttccctcat cataagtcgg tagcgcaatg gtcacttttg cattaatcac gccctccatc    10860
tgactcagca ttccttcaat tctttgttct tttaaaaaat taatcttctg ctgttcttcc    10920
tggggtgata ccactaactg attagccgga aacatcttat ccgccgttgt aaactgacga    10980
tgcggataac cgttaagtct aagtagctca accgcattaa taaactgcga ctgctcgaca    11040
cgtaaggtaa caccgtcctc ttcctgtttt ttttccgcat caatatgatg ctgcataagt    11100
aatgccagca tttgattcgc ctcatcctct ggcaatgagc gataaagatc cacatcacat    11160
gccgtaagaa agaacgtaag gacagtaaga aatactatac gatgagcctt catgccatgt    11220
tatccagctt attaagcgct tgcgatgctg cgcctgatat tctggcaaga taatcgacgc    11280
ctaccgttaa ctgcatataa tccatttgtc tggtcaacat aacctgcggt aataaagcac    11340
tggcgttact ggtggatgct tcatctttca gcaattgttc aaaaaaatta atttgctcct    11400
```

```
ggctcggttc tgcagaggac tttacataag attgagtgct tacaggcact acgctcatat   11460
cagaaatatt caattttcaa acccctcatt tggtgcagga ataacagac gcagcgccat    11520 agcctctggc aaatctatat ccgataaaat tttcgcggct tttagcggct catttaaacc   11580
cgccaacaat aatgccagac ataccaactg taatttttta tccggaacaa taaccgttag   11640
cgctggtaac atcgcatgta cctgggaaat caggctatgg ttaacgcccg caaacatgat   11700
ttccagcagc aaccgtcgaa catcgtcgct aataacttca gattttagca atgattccac   11760
taagcatatc cttgatcatt ttgatcagtg aactttcgta attaataaat gtagaatact   11820
gctgtaaggc aaattgcgct ttaatcatcg attctgggtt gagcaaatca ttaccattca   11880
ttttgtcatt aatggcctgg cctgcctggt gcgccatgtg ggagagcata tccactaatt   11940
gtgcaatatc cataatgctt ttccttaaaa taaatacatc gtaaggatac tgcaacata   12000 gcaaaattta gaaagcaatg aacatccggt atatacctga aaacgattac tccggcgcac   12060
gttgttctgg cgttacctga gccagcaaac gatataatgg gctgctgacc tgcataccgg   12120
tcattgccat cccatccata ccgaagcgag taaaactcat tagtccatag gtaatatcat   12180
taagacgctc taataaatga ggctgtagtc ccaaactacc actccagtat gaatgcgtca   12240
ttaccgtcgc ggttaaggct aatctaccgc ccagggagac ggctttagca atcgccatac   12300
ttttgcgttg attggcgaaa caattagcaa tataaaaaac ggcattgcct atactgtcgt   12360
gagccatagg caaatgatgt ttatgatggt agataagaca ggcgacatcc gcgatggcaa   12420
tagcaaggcc aatccctgcc agggctacga gcggcgcgcc tccaccactt agcactgtta   12480
atgctattcc agcggaacag cataaaatct gtccgcccaa ataaccgtt tgccaactaa   12540 aaatttcttt tggaaaacac tctatcactc gtttcgcaag tccggccaat aaccgctctt   12600
ttccttgttg aggacctatt ctaccactct ccatattggt ttccggatgt ggcaatgagg   12660
gacatggagg tgattcctca ggcgcgttaa caggacgttg ccctcctacc tgagcatttg   12720
ggctaacagg tttcatggtt ctccccgaga tgtatgacca gaactgtcca ttaatgcagg   12780
tgcagtagca gattgacaga gcgctgccat ttgttccgcc aataacgcac tgggatcggc   12840
ataaagttca tcaacagaat tttcctgatc gtcgccagag gggcgggcaa ggcaataatc   12900
cagtaccgca cctatcgccg tcaggctaac ggaggtaatt acactcccca tgtccaaaga   12960
ggccgcaata ttttcagccg cgggcagtgg aaactgtagg ggtaaaacca acatagaaat   13020
agcgattcct gaacgtatta ataaagaaag acaattagca agggtgttag cgcagttaag   13080
acttgcccca catttaagg ccagcgcact gaccacaaga gcaacgctat cactggcggt     13140
ttgtaatggc tccttttgct gacatatcga ttgataatta tgatacgcac agcaagcatc   13200
cccaatagca atcacgagcg ccgccccgc aagaatagca atgggtaatc ctgccccgcc    13260
agaaattacc gctgcagcaa ccgataaccc aaacacgact gtcgcaccca gcgcacgaat   13320
agtgtattgc ataaaatgta tagcataatc cctctgctgc cttatttgtt caggcgtaag   13380
cagcacaggg gctgcggggg taccaggcgc tggaatttca ggggaggaa acgatacctc     13440 cttcgcttgt atatcggaag gaggactatt accatcgact atattacttg ccgctgacgg   13500
aatatgaatt ttcatatttc gttctgttat ttaagcaata agagtatcaa ccattatttg   13560
cgcattctgg cgaatctcac tccatgaggc atccgcataa ctcatcttga ttgcggtttg   13620
aaaagcctct ctcgccaacc cgggttcccc catcattttg agacagacgc ccgtttggta   13680
aaccggttct ggatggctgg catccagcat caaggcatgt ccatagaaat taatggccgt   13740
tgtgtattct ttaagcatca tccaggtgcc agccaatgca atatgggcac gccaactcca   13800
```

```
tggctgggcc atcaccagcc aactaaaatc gattacggcg cgcgaataat cccctcctg    13860
ccatgaggcg taaccactgg cataaacggt ttccggatca acggataata gctgtttcag   13920
aatgtcttcg ggtattttat ttttctgatc ttctttcatc atcataccta ttgattgtta   13980
ttttcacgtg ataatgattt acgttaggaa ggtcatttaa aaacgtcgct ggataagatg   14040
ctcggcggat aaaactgtcc agttatcgcc atcaagctgt gtaaaggtcg ctcccattac   14100
tgtcaggatg cgcaataatt tcctgcgtag catggctttt ttttcatcca gaacgtcggt   14160
gattatcaac atctttaaac atgttaactg cgggtgatgc acaaatatcc cgcgtaaaag   14220
tcccagtaag tgaaacaatt gctgtggtcg aggttgcccg ggcgtcaggc gcctgaactc   14280
acaaataatc atttcttttg cctcaatacg atagatcacc aggtaaggcg ataatataaa   14340
ctgctgccca gtaatatggc ggtctcccc taaatatgca ggctcagtaa acacctgatg    14400
ccgacgcaac cattgctcta tttcttgcac catgtttacc tcgttaatgc ccggagtatt   14460
tcagcaagaa ccgtgaccag tgacgacccc acgccgatga tttgctgcat aatttcagtt   14520
gctttctccg taatttccgt cagggattta ttataagatt gggcccccatt ttgttgcagg   14580
tcggcaatcg ctttatcttg atcactttga cgttgcgcta caccagcccc caggcccatg   14640
acgcccccag ctgtgtggcc tacggcttga cccgctataa gaccggtttc cccgcctacg   14700
gccctaatc ctatcgtcag tacacccgac aacattgcgc cacccgcagt aatcattgat    14760
gctctaaacg cttcatcaat tgttttcatt tgcgtctgta aaacattgac ttgcagttcc   14820
caggccagcc gttgttttc tacgttatag ctgcgcatga tatcgcgcag cttttttggca   14880
agctccatta gcttcatcca gatatcatca ataacagaa gcattgattc agtacccatt    14940
ccctccccgg agggagatgg agtggaagaa ggtgttaaca aggaaggcgc tggtaatacc   15000
agtgctacgt tactcgcttc catatttta tcctcagatt aagcgcgata gccagctatt    15060
ctcgcctgaa cgctactata gtgatcaatg gtatctaata catctctaag cgcggcaccg   15120
ctcccccttat aaagcttctc taagcgtttt tgttctatct ttttctggtt ttctgtttgt   15180
tgcattatga aatccagaaa ccgttgctga gttattaatt gctctatttt cttttcgatc   15240
ttcgcttttt ctgtgttaac catgccagta ttcatctgac tggcgccctc ggttgcacat   15300
ctgatagcct gtaagccttt aaatgaacaa tccctcagta aggcatacag gatttttttg   15360
aacatattga agagaacttt attacggaat ttttttaaca ggaactttcc accttcttgc   15420
acacatttt ccagggcttc ttttgccgct tcttttgcca tggctttcac cccctctttc    15480
gtaaagcttt ttcccgcgct tcgcgtcata ttattttcta cgttacgaga aaactcggca   15540
gcctcctctg ccatctcatt cgccatagcc atttcacgtt caagcggctc aaattgtttg   15600
gaaaaacttt cgctcacttc ttcgccaaac ttttcagcca actcctctat ttctgcttcc   15660
cctgcaccta ccatacgctc aaccacttcc tcgccaaaac cggagtcaag cacttttgca   15720
gctgcgccag ataaacctct cgtcgccata aaagcacggc caatctggaa acatccagt    15780
gccagcgcga cggcttcaca accaaattga atcttacttg tcacgtcaat aattgcctga   15840
caggtatcgt ggtcagcacc gcacatcatt gccgtttcgg ctccggcttt aaccattcct   15900
gcacaaccta cggctatata agctacgccg ctagccattt ctgcgggatt accggacaga   15960
aacccctcca caacttttaa ggagccaatc acagtttcaa atatgccggt aatccagtca   16020
aaaatagcgc caaaaatgcc cgctttacgc gctttatcct cctgctctat cgctttctgg   16080
atctgctcct gatactcctt tacctgctta tcacgtaatg cattttgcac ctcagttgcc   16140
cgctcaagct gttggcataa cgattgagcg ttattaccaa aaacgctgag tattaatgtc   16200
```

```
gtcatcaaca ttgataaaac cgcgggattg gtctgcaaaa agtcaggcaa tgatagacgc    16260
ttatgatttc cgggtacggc atcaagcagt tgcttcaacg cattgcttgc ctcctgaaga    16320
ctaattttcc ctgataacag gcacgcggcg ttgccatcgc caaaagtaga attcacacga    16380
tgccggcgct ttcccagcga acccgaggaa acgcaactga cattgcttaa gtgatgatgt    16440
gttaaggcgg ttactcctgc ggtgctgtcg ctattactgt gaattcgatt cattttagc     16500 tcctgtcaga aagttgctgt aacatctttt ctgcacgctg tcggagaatt tgatgttcac    16560
tgacctcgcc gcaaatacgc accacggcct ttaacgcttt gattgcataa cagacgttat    16620
cacacgcgag atagcattcc gctgcgggcc atggcgcctg cggcgcatca atcttaattt    16680
gtgccgcgcg tccataagcg tatatcgctt cccccaatg tttttgagcc tggcagcatt     16740
cccctaacct aaaccagtag tcaaatgacc aggcatcata tatcgtcaac aattgaaaaa    16800
gtcgcgctgc gccggcgaac tcttttacct ccataagctg catggcatag cgatacagag    16860
tattaagcgg ctgtgtaaca tcgtcatcca acaacatacg cagcgagccg ccacgccgga    16920
aaaaccgcat cgtgtcatgt gcctgttgta gggtcgggtc ttttttcatg agtacgtttt    16980
ctgcgctatc atactgggaa tttccccca cttactgata agccctgtca gttgggtaag     17040
gacagcgtta agctcctgag acattttttg aattgttatc tgcccctgac tcataagatc    17100
ggtattccgg ttggcgtcat tatccaaagc cgctttgatc gcctgtaggc caccttatc     17160 cagcttccca tgatcgccat atttagccat ataatcatca atggtcatac catcgatgag    17220
aataccatta tcacgcatgt atttaattac atcctcaggc acctcctctt tggttttagc    17280 atccccttg gctgctttag caatcacctc atccatctca tttgactttt cctgggtatt     17340
tctggcacgt tcagcgttct tctggacttc aataaattta ttatttgcga tatcctgaat    17400
aaccataagg agaataagca aaacaccata cccttcggca aacggatttt gctgggataa    17460
gtcatcctgg ctcccggtat cagcgttgct gacgccgaag ctattttaa acacaatagg     17520 gttttgactt ccccataaga tgtttcctga agacattatg ctttaccttt ttgttttcc     17580 tgacggtatc tccaccgggg cttgagcatt aagttgtttc agtcgtactt caagttgttt    17640
aaacaaactt actattttct ttaaatcctt ctcggcctcc tggttaaccc cggcaacgcc    17700
ttgtggaaat aggttttgaa gaatactctc tgtctctctg ctctttttgg ggctctctgc    17760
cctttcagca agctgttgac tcaccttagc ccggatttgg tgaaattttt taagacagtg    17820
atttagctgc atgtaacttt gctctaaatc acgatattca ctaaacgcag cctttttctt    17880
tatcattatt cccctccata tacacgtatag ataattaacg tgctaactaa gagcctatcc    17940
cattagggct attttacttg ccatttgaa cctgggcagt gctcaaaatc ctcacgtact      18000
acgtgtacgc tccggttttt gcgcgctatc cgtgtccaaa ctggctgcgc caattaacgc    18060
ctggtgggat aggctctaag atatttttac tttactcttg ctcactcact acaagtgcgc    18120
tgttatggta acgataataa ataatgttga tgatattttc ggcctgctcg atcgcttcaa    18180
gcaataaggt gttttgctga tattgctgcg gatcctgtaa cttgccgttg ttctctccta    18240 actgttccg ggcagccctt aattgtaaaa ttatgccttt ggcctcttca cgcgaatgaa      18300
gcagcaaatc ttctaaccgg gtcaaagttg tcattttcca ctcacttaaa atctaatgga    18360
tagttaatca aagtatcata atgtttaatc gttaccacat cggcactcag atggacaatt    18420
tctcccccat tgggtaacaa tgccctaca cgtaaacgct ctttattcgt cagtaataag      18480
taattaccat ggcgactctg tacaaagcca gccactggcg caggcagata cttgctttca    18540
tcatgggaag gcgcaatatc ctgataaatt aaagaaagag cgggatcctt tttctttaat    18600
```

```
gctgctaacg tttcttgcaa aatgcgttga tgagattcat ccagtacacc actgataaca   18660
aaagagcgcc gcattggcgt aacattgaca agccccacta aaccgttctc tattatcgca   18720
gaaataatat catctccctg agactgatga gagtgactaa tctgccagtg caataacccg   18780
ggaatatctg caagtaatgg ttgaaccttca cgccattgct gatccatttg tatatcatca   18840
tgaattaaca cgctccccgg cccttcgctg gatacttcag catgcgggta acccatttt    18900 atcaaaacat cctgcacttc tcgtaccaat aagtcatcac agattacacc atcccgatac   18960 atgaccccc atgattcgag agtcgctctc accttttgca tctgttcgct tgacgagcaa    19020
taaccggaca actgcaggct gccatcttct ttccattgcg cccgcacata atgaatattg   19080
cttttgtcta ataaaaactt aacccgcaaa ggtaagtcat ttaccgtttc aggctgacca   19140
ctaatactta acaggacacc cattccaccg atgaaaatca agaatacgcc agccaaccac   19200
cagtaccctg atctggaaac gggtatttga taatcagcaa gttcacaatc ctgtttacca   19260
aacgcgatag ccactcccgc aacctgcaaa accccactgg atggtagcgg cttatttgga   19320
ttaaatctgc ggccattaac tctaactctg gctttcccgg catcaacaaa taaattatct   19380
gcctgttctc tcagaataat ttttcattt atagtaagcg gaatacaaat atcgcatcct    19440
ttctccccca gtgacaggtt accttcattc agccatactt cccggccttg taaaacgtga   19500
cctaaaaaac gtattttcca ggaactcttt ggattaacca tgagatatgc cattatttac   19560
tactgaggct ttaatcaaaa aaagcctgat tacactatgt acttgagtcg tatcattgcg   19620
aaacaaatgg cctacgacag gaatatcgcc caataaagga attttatttt gcgagtggat   19680
ttgtttacct tgtttaaatc ctcccagcaa tagactttgc ccggccaata atgtggcctg   19740
cgaagcaatt tcagaatttt gcacttcggg cagcgggtct gtttcgcttt gcgtatcact   19800
ttgttgtcca tcctgaatat taagatcaag cattatttt tgcgtgccat tatcatttaa    19860
caagcgaggt gtaacgcgca acaaagaacc cgtagtgatg gattcaagtt tagccacttt   19920
ttctccctgc agtttggtat agaaagtaat atttttatcc agcacagcct ggatattatt   19980
taaagtcacc acagatggct gggaaagtac ataagcctga gagcttttt ccagggcatt    20040 caaacgcacc ataaagttg aggtatcgct gattaccgtt gaaaaaccgc tagcaccacc    20100
gtcattcaaa cctgtattga acgcaatttt cttgccaccc agcgacactg ccgttcccca   20160
gtcgatgcct aactggttaa tatctccagc attaacatcg ataattttca ccgaaatctc   20220
tatcatctgc tggcgttgat ctaattctgt gataagtttc cgatacccgg ccatattgga   20280
cgcataatca cgaacgatca ctgcattctg gcgtgggtcg gcagcaaaca tgggcaatgc   20340
ctgtgtagcg ggtgaaccat tgttcgtcga tgacgccggt acgctggttt tactcatctc   20400
acgcaataca ctcacgaccc ctggaaccac gacggactga tcgcgatatt ggtattgggt   20460
atccatcgca gtggcatact aagcgtgta tatacttaca ctcaccgcac tgtctttcg     20520 tttgattaac gcattatcca gcactgaagc taattgacta atacgagtca ggcagctggg   20580
aacaccgctc acctccacag ctttggtacc ggtaatttct ttaacctcgc atcccggtga   20640
tgaaagaata ttctggctgc gtaagtaatg aatgaaccgt ccagtagata aaatattgaa   20700
agtgataacc tgatgtttta ataacgatgc aggatataca tataacatgc tgccatcaaa   20760
ccaggtaagc aaatcatatt gtgctgccag gttattcaaa atatcgaccg gtggtccagg   20820
cggaattttt ccactaaatg tagctgttat caatgggcta atagtaatag ccgtatcata   20880
gttctctgag agcagatgta aaacctctgc taatggcatt tgtctggcat aaagggtgaa   20940
gtcattacct ttccatgata actcatcact ctttgctgta ttgagtataa atagtaaaat   21000
```

```
taagattaaa cgtttattta ctaccatttt ataccccacc cgaataaagt ttatggtgat    21060
tgcgtattac attttttaaa atgcaagtta aagccaggtg ttttctatc tcaatagcaa    21120
taagctcaga gctactactt gtggtataat aaccgtttaa ccatcccca tccgctgtga    21180
gctgtatagc ataatcatgg acgtccgggt gtgctgcaag cagtagtgtc acataggcaa    21240
gacaaggctt aggtaagctt tccaggtcat ttaagaacaa agaaatagaa aatgcttctg    21300
agaaaatttc tcctctggca ggatgcccat caatagtcat tatccaggat cggctattac    21360
cttcggcctt gatatcctga attaatggaa tgccttttaa aactgccagc atgaatccct    21420
cctcagacat aaatgggagt ttctatcaaa ttcgctcaca accacatccg taaaaagcct    21480
gattcacatt tatttcgact atacttttct tgtacaatat caggatgctg tctacatata    21540
ccttgtcaca ggcgattcta tcattcggat tttccgataa attcacaatt acattttcag    21600
cactgacata aaaacttaca atttgaaaaa tcatttatta aatgaactgt tacgatgttt    21660
ttacatcgcc atcttattaa aaagtaattg tagtcatcga ctgggttata tatgaagaaa    21720
tttatcttcc taatgataac accatcgatt aatcttctga tgaaactata tgtactgcga    21780
tagtgatcaa gtgccaaaga ttttgcaaca ggcaactgga gggaagcatt atgaatttgc    21840
tcaatctcaa gaatacgctg caaacatctt tagtaatcag gctaactttt ttatttttat    21900
taacaacaat aattatttgg ctgctatctg tgcttaccgc agcttatata tcaatggttc    21960
agaaacggca gcatataata gaggatttat ccgttctatc cgagatgaat attgtactaa    22020
gcaatcaacg gtttgaagaa gctgaacgtg acgctaaaaa tttaatgtat caatgctcat    22080
tagcgactga gattcatcat aacgatattt tccctgaggt gagccggcat ctatctgtcg    22140
gtccttcaaa ttgcacgccg acgctaaacg gagagaagca ccgtctcttt ctgcagtcct    22200
ctgatatcga tgaaaatagc tttcgtcgcg atagttttat tcttaatcat aaaaatgaga    22260
tttcgttatt atctactgat aacccttcag attattcaac tctacagcct ttaacgcgaa    22320
aaagctttcc tttataccca acccatgccg ggttttactg gagtgaacca gaatacataa    22380
acggcaaagg atggcacgct tccgttgcgg ttgccgatca gcaaggcgta ttttttgggg    22440
tgacggttaa acttcccgat tcattacta agagccacct gccattagat gatagtattc    22500
gagtatggct ggatcaaaac aaccacttat tgccgttttc atacatcccg caaaaaatac    22560
gtacacagtt agaaaatgta acgctgcatg atggatggca gcaaattccc ggatttctga    22620
tattacgcac aaccttgcat ggccccggat ggagtctggt tacgctgtac ccatacggta    22680
atctacataa tcgcatctta aaaattatcc ttcaacaaat ccccttaca ttaacagcat    22740
tggtgttgat gacgtcggct ttttgctggt tactacatcg ctcactggcc aaaccgttat    22800
ggcattttgt cgatgtcatt aataaaaccg caactgcacc gctgagcaca cgtttaccag    22860
cacaacgact ggatgaatta gatagtattg ccggtgcttt taaccaactg cttgatactc    22920
tacaagtcca atacgacaat ctggaaaaca aagtcgcaga gcgcacccag cgctaaatg    22980
aagcaaaaaa acgcgctgag cgagctaaca aacgtaaaag cattcatctt acggtaataa    23040
gtcatgagtt acgtactccg atgaatgcg tactcggtgc gattgaatta ttacaaacca    23100
ccccttaaa catagagcag caaggattag ctgataccgc cagaaattgt acactgtctt    23160
tgttagctat tattaataat ctgctggatt tttcatgcat cgagtctggt catttccat    23220
tacatatgga agaaacagcg ttactgccgt tactggacca ggcaatgcaa accatccagg    23280
ggccagcgca aagcaaaaaa ctgtcattac gtacttttgt cggtcaacat gtccctctct    23340
atttttcatac cgacagtatc cgtttacggc aaattttggt taatttactc gggaatgcgg    23400
```

```
taaaatttac cgaaaccgga gggatacgtc tgacggtcaa gcgtcatgag gaacaattaa    23460
tatttctggt tagcgatagc ggtaaaggga ttgaaataca gcagcagtct caaatctttta   23520
ctgcttttta tcaagcagac acaaattcgc aaggtacagg aattggactg actattgcgt    23580
caagcctggc taaaatgatg ggcggtaatc tgacactaaa aagtgtcccc ggggttggaa    23640
cctgtgtctc gctagtatta cccttacaag aataccagcc gcctcaacca attaaaggga    23700
cactatcagc gccgttctgc ctgcatcgcc aactggcttg ctggggaata cgcggcgaac    23760
cacccccacca gcaaaatgcg cttctcaacg cagagctttt gtatttcccc ggaaaactct    23820
acgacctggc gcaacagtta atattgtgta caccaaatat accagtaata aataatttgt    23880
taccccctg gcagttgcag attcttttgg ttgatgatgc cgatattaat cgggatatca    23940
tcggcaaaat gcttgtcagc ctgggacaac acgtcactgt tgccgccagt agtaacgagg    24000
ctctgacttt atcacaacag cagcgattcg atttagtact gattgacatt agaatgccag    24060
aaatagatgg tattgaatgt gtacaattat ggcacgatga gccgaataat ttagatcctg    24120
actgcatgtt tgtggcgcta tccgctagcg tagcgacaga agatattcat cgttgtaaaa    24180
aaaatgggat tcatcattac attaccaaac cagtgacatt ggctacctta gctcgctata    24240
tcagtattgc cgcagaatat caacttttgc gaaatataga gctacaggag caggatccga    24300
gtcgctgctc agcgttactg gcgacagatg atatggtcat taatagcaag attttccaat    24360
cactggacct cttgctggct gatattgaaa atgctgtatc ggctggacaa aaaatcgatc    24420
agttaattca cacattaaaa ggctgtttag gtcaaatagg gcagactgaa ttggtatgct    24480
atgtcataga cattgagaat cgcgtaaaaa tggggaaaat catcgcgctg gaggaactaa    24540
ccgacttacg ccagaaaata cgtatgatct tcaaaaacta caccattact taatattatc    24600
ttaattttcg cgagggcagc aaaatgaaag aatataagat cttattagta gacgatcatg    24660
aaatcatcat taacggcatt atgaatgcct tattaccctg gcctcatttt aaaattgtag    24720
agcatgttaa aaatggtctt gaggtttata atgcctgttg cgcatacgag cctgacatac    24780
ttatccttga tcttagctta cctggcatca atggcctgga tatcattcct caattacatc    24840
agcgttggcc agcaatgaat attctggttt acacagcata ccaacaagag tatatgacca    24900
ttaaaacttt agccgcaggt gctaatggct atgtttttaaa aagcagtagt cagcaagttc    24960
tgttagcggc attgcaaaca gtagcagtaa acaagcgtta cattgaccca acgttgaatc    25020
gggaagctat cctggctgaa ttaaacgctg acacgaccaa tcatcaactg cttactttgc    25080
gcgagcgtca ggttcttaaa cttattgacg aggggtatac caatcatggg atcagcgaaa    25140
agctacatat cagtataaaa accgtcgaaa cacaccggat gaatatgatg agaaagctac    25200
aggttcataa agtgacagag ttacttaact gtgcccgaag aatgaggtta atagagtatt    25260
aa                                                                  25262
```

<210> SEQ ID NO 3
<211> LENGTH: 6053
<212> TYPE: DNA
<213> ORGANISM: Artificial Sequence
<220> FEATURE:
<223> OTHER INFORMATION: spvRABCD operon

<400> SEQUENCE: 3

```
atggatttct tgattaataa aaaattaaaa attttcataa cactgatgga aacaggttcc     60
ttcagtatcg caacatcagt actgtatatc acccgaaccc cgctgagcag ggttatttca    120
gacctggaaa gagagctgaa acaaagactc tttatacgga agaatggcac tcttatccca    180
```

```
accgaatttg cacaaactat ttatcgaaaa gtaaaatccc attatatttt cttacatgca    240
ctggagcagg aaatcggacc tacgggtaaa acgaaacaac tagaaataat atttgacgaa    300
atttatccgg aaagtttaaa aaatctgatc atttcagcac tgaccatttc cggccaaaaa    360
acaaatataa tggggagagc cgttaacagc caaataatag aagaactgtg tcagacaaac    420
aactgcattg ttatttctgc cagaaattat tttcatcggg aatcgcttgt ctgccggaca    480
tcagtggagg gtggggtcat gttatttatt cctaaaaaat tctttctctg cggcaaacct    540
gatatcaaca ggctggccgg aacacctgta cttttcatg agggggctaa aaattttaat     600
ctggacacca tataccattt ttttaaacag acactaggta ttaccaaccc tgcattcagt    660
tttgataacg tcgatttgtt cagttcactg taccggttac aacaagggct ggcgatgtta    720
ctcatccccg tcagagtctg tcgggctctg ggattatcaa cagatcacgc actgcacatc    780
aaaggcgtag cgctctgtac ctccttgtat tacccgacca agaaacggga gacaccagat    840
tatcgtaaag ctataaaact gatacagcag gaactgaaac agtccacctt ctgaccttat    900
gcagcgtaag ggccgcaaca cctgtattca cggcatttgc cagattcaga ttgtcagcaa    960
tccccatcct ccatagcggt agttcaccgc ggagcatgga gtaaaccggc tggtcgccgt   1020
caatctgaca cagaatcagt ttgatgctct ggtggattac ctaaaacatg gcattaacg    1080 cgctggctca cgccacttta ctgaagaaac tgaataacgg tgactatgac ggcgcagcga   1140
atgaattcct gaaatgggac cacgccagcg gtcaggttgt tcccggcctg acccgacgcc   1200
ggagcgctga acgttgttta ttcctgagtt aatttgttgt gccatctttg cacaccggga   1260
accgcgattc cgcacagcag aaaaatagca cataaataaa ctcaatataa gccactcatt   1320
ttctggcaat acaaaataat tccccctgcag acattatcag tcttcaggat ttcattctgt   1380
ttattttcag gagtcatcat tatttatgaa tatgaatcag accaccagtc cggcactttc   1440
acaggtcgaa accgccatcc gggtcccggc agggaatttt gcaaaatata attattattc   1500
cgtgtttgat attgtccgtc agacccgtaa acagtttatt aacgccaata tgtcatggcc   1560
gggatcccgc ggaggtaaag cctgggacct ggcgatgggc caggcgcagt atatccgctg   1620
catgttccga gaaaatcaat tgacccgcag agttcggggg accttgcagc agacaccgga   1680
caatggcacg aacctgagca gttccgctgt cggcggtatt cagggacagg cagagcgtcg   1740
gccggacctg gccaccctga tggtggttaa tgatgccatt aaccagcaaa taccgaccct   1800
gctgccgtat cattttccac acgaccaggt ggagttatct ctgctgaata ccgatgtgtc   1860
gctggaagat attatcagcg agagcagcat tgactggccg tggttcctga gcaactcgct   1920
gaccggcgat aacagtaact atgccatgga gctcgccagc cggctgtcac cagagcagca   1980
gacactgccg accgagccgg acaacagtac cgccactgac ctgacctctt tttaccagac   2040
caatctgggg ctgaaaaccg ccgactatac gccatttgaa gcactgaata cctttgcccg   2100
acagttagcg attaccgttc ccccaggtgg aacagttgat tgcgggtact ctgcgtgcca   2160
gccggcagtt tagcttcccg cgctaccaga gtagtgagca gcagaccatt ctgcagaatc   2220
tgagcgacgt cattgttcag gtgcattcta ccgcgctgta cggcggcagc acttttgaac   2280
aggccgtaga gcagacgctg taagcagaaa atatacctgt ccatcgtcag acggccagtt   2340
tcaggagata gtgtatgttg atactaaatg gttttttcatc tgccacttta gcgctgatca   2400
ctcccccttt cctgccaaaa gggggcaagg cgctgagtca gtcaggccct gacggcctag   2460
ccagtataac gctgtctctg cccatcgcg ccgaacgcgg ctttgcgcct cgctggcgc    2520 tgcactacag cagcggtggc ggcaatggcc ccttcggcgt gggctggtcc tgcgcgacaa   2580
```

```
tgagcattgc ccgccgcacc agccatggcg tgccgcagta taacgacagc gatgagtttc   2640
tggggccgga cggagaagtg ctggttcaaa cgctcagcac cggtgatgcc cccaatcccg   2700
tcacctgctt cgcgtacggt gacgtatcgt tcccgcaaag ctacacggtg acccgctatc   2760
agccccgcac ggagagcagt ttttatcgcc tggagtactg ggtgggcaac agcaacggcg   2820
atgatttctg gttactgcat gacagtaacg gcatcctgca cctgctgggg aaaaccgccg   2880
cagcacgcct cagcgatccg caggccgcct ctcatacggc gcaatggctg gttgaggagt   2940
cggtgacccc tgccggcgag catatctatt actcctactt ggcggagaac ggtgacaatg   3000
tggacctcaa tggggacgag gccggacgcg atcgcagcgc catgcgctat ctcagcaagg   3060
tacagtatgg caacgcgacc cccgccgccg atctgtacct ctggactagc gccacacccg   3120
cggtacagtg gctgttcacc ctagtgtttg actacggcga acgtggtgta gatccacagg   3180
taccgcctgc attcactgct cagaacagct ggctcgcccg ccaggatccc ttctccctgt   3240
ataactacgg ctttgagatc cgcctccatc gcctgtgccg ccaagtcctg atgttccacc   3300
actttcctga tgaactgggt gaagccgata cgctggtttc ccgtctgctg ctggagtatg   3360
acgaaaatcc gatactgaca cagctttgcg ctgctcggac gctggcctat gaaggcgacg   3420
gttatagaag agctcctgtc aacaatatga tgccaccgcc accgccaccg cctcctccga   3480
tgatgggagg taattcatct cgaccaaaat caaaatgggc gattgtagag gaatcaaagc   3540
agattcaagc tctgaggtac tattcagctc aagggtacag tgtgattaat aaatatttac   3600
gtggggatga ttatcctgaa acacaggcaa agaaactct gctctccaga gactatcttt   3660
ccacaaatga acccagtgat gaggagttta aaaatgccat gtcagtttat ataaatgata   3720
ttgtggaggg attaagttca cttcccgaaa cagatcacag agtcgtatac cggggcctga   3780
agcttgataa gcccgcatta tcggatgtgc tgaaggaata cactactata ggtaatataa   3840
taatagataa agcttttatg agtacatcgc cagataaggc atggataaat gacactattc   3900
tcaacatata cctagaaaaa ggacataaag gtagaatact cggagatgtt gcacatttta   3960
agggagaggc agagatgctt ttccctccaa atactaaact caaaatcgaa agcattgtaa   4020
attgtggatc ccaagacttt gcaagccagc ttagtaagct gagattaagt gatgatgcaa   4080
ctgctgacac aaacaggata aaaagaataa taaacatgag ggtactcaac tcatagatac   4140
taagaatcta ttccagaagt ggtatgagcg gcctagctct ataaggggtt atactccgga   4200
accccagatt tttccgtcac cctaggcccg caaagtagtg catctaaact tttgccatta   4260
cccttcttta actttctgct cggaacggac cgaaatatca ttttttcgcc tgataaaaaa   4320
tgaggttttc tggataacta atcgttttat taaaaaaaac tgagaattta tatctaataa   4380
tatggcgata tatccatatc gcaaaggaga tttcccatgc ccataaatag gcctaatcta   4440
aatctaaaca tccctccttt gaatattgta gctgcttatg atgggcggga ataccatct   4500 acaagtaagc acctgaaaaa taatttcaac tccttgcaca accaaatgcg gaagatgccg   4560
gtatcccact ttaaagaggc gctggatgtg cctgactatt cagggatgcg ccagagtggt   4620
ttctttgcta tgagccaagg ttttcagctg aataaccatg gttacgatgt tttcatccat   4680
gctcgtcgag aatcacctca gtctcagggc aaatttgccg gtgacaagtt ccacatcagt   4740
gtgctcaggg atatggtgcc acaagcattt caagcgctgt ccggattgct gttttcagag   4800
gacagtccgg tagataagtg gaaagtgacc gatatggaga aggtcgctca acaagaccgt   4860
gttagcctgg gcgctcagtt cacgttgtat ataaaaccag accaggaaaa ttcgcagtac   4920
agtgcgtcgt ttctccacaa gacacggcaa tttatagagt gtctggaatc cagactatcc   4980
```

```
gaaaatgggg ttatttcagg acagtgtcct gagtcagacg ttcatcctga aaattggaaa       5040
tatctcagtt atcgtaatga actacgaagt gggcgtgatg gtggcgaaat gcagagacag       5100
gctttacgtg aggaaccgtt ttatcgtttg atgacagagt aagtatgggt ttggggagca       5160
acggaacagt aaacgccgtt aaacaactat tttaaatgct cattaattta ttaatcaata       5220
aattacaaat tttcattgaa ggctccccccc ttactgacga attccggcac cgtaaaggaa      5280
taacgctcat gcatattgat gtgtccgcac tgtaatggtg aaaattacat aagcaagagc       5340
gttttttgaa aaatattata tttaatgttt tgtaatatgc attttattga ggtagtgtaa       5400
ctatgagagt ttctggtagt gcgtcatccc aagatataat atcacgtata aattcaaaaa       5460
atatcaataa taatgattca aatgaagtca agagaattaa agatgcgctt tgtattgaat       5520
caaaagagag aattttgtat ccaaaaaatt tgagtctaga taatttaaaa caaatggcta       5580
gatatgtaaa taatacatac atccattact ctgggaactg cgttttatta tcagcgtgtt       5640
tacattataa catacatcac cgacaggata tattaagttc gaagaacact gcctctccta       5700
cagtgggatt agacagcgcc attgttgata aaatcatttt tggtcatgag cttaaccaat       5760
catattgttt aaattccatc gatgaggtgg aaaaagaaat attaaaccgt tatgacatta       5820
agagggaaag ttcttttatc attagcgcag agaactacat agctccaata attggcgaat       5880
gtagacatga tttcaacgct gtggttatct gtgaatatga taaaaaacca tatgtacaat       5940
tcattgattc ttggaaaaca tccaacatac ttcctagctt acaagaaata aaaaaacact       6000
tctcatcatc agggaattt tatgtcaggg cttatgatga aaaacacgat tga              6053
```

<210> SEQ ID NO 4
<211> LENGTH: 1590
<212> TYPE: DNA
<213> ORGANISM: Artificial Sequence
<220> FEATURE:
<223> OTHER INFORMATION: faeHIoperon

<400> SEQUENCE: 4

```
atgaaaataa cgcatcatta taaatctatt atttccgccc tggccgcgct ggccctgttt         60
tattccgcag caccccgggg ccgaattctt gacggcgggg aaatacagtt tcaccgtctg        120
gtcactgacg aggctccgaa atggacctgg caggtgggct cccctgacca gacatgggcg        180
gtggataccg ctgatgcccg tacagcgaac ggacaactgg ttttttgattt acgcggcaag      240 ggctccctgc cgtttctgga aggccatctg tatgaggtgg cagagcgcgg tggtcccggc        300 ttcaccccctt ttatctcctc cagcagtaac gggcagccgt tttccgtgac ggatggcggc      360
acgacgacgg cgcaacactt ccgcgcctct gtcccggtac gtaacccgga gaacggtcac        420
gtggcgggac agctttcttt cacccttgac cagggaatgg ccgtcagcgc cggacaccag       480
gaagacgggg cggttctacc ggcagcgatg tcgctcgtaa acgggcagag cgtgacgggt        540
gtgcaggccg gcaccctgcc gcagtggctc aaaaaccgtc tgccttccct gctgatgctg        600
aaccggggct tcggtaacgg aatgagcacg gcagataacg gtcaggttat cagtcagggc       660
gtgctggctg acgccgggt gacccggctg gcggcggcct atgcgtccgc cgtctctcggat      720 tttgagctga cgctgccggc agaaaaacacg ccggtgcagt ggcaggccgg gctgagtgtg      780
acggtgacgg tccagtaaag aacgggcagg agaggaaga acacaatgaa acgaatgacg        840 atttttactgc tggccgccag tctgctgccg tcctgtgtgc tggcgtggaa cacgccgggg      900
gaagacttca gcggagagct gaagctgggc gggccggtga ccagcacccg taatccctgg       960
gtctggaagg tcggggaagg gaacacacag ataaacacga agctgtctc tgtcctgcgc       1020
```

```
agtggggagg aggtaatacc ggttcccctg ccggccatga cggtcctgct gggaaaaact    1080
atcctgacca cccgggccgg ccgggagggg cttgcgccgc aggtgacgta cggtaaggac    1140
acagagggtt ttgcactgac gtggacggca ccgggtatgg catcggtgac actgccggtg    1200 acggggagg gaaatgtccg taccgggaca ttcaccttcc ggatgcaggc ggcgggtgtg     1260
ctgcgccatg tcctggggaa ccgggcggag tatgccgggc tgtatggcga cctgcagggc    1320
aacggcttgc cgccacagac gcaggtgatg ccggcagggc agacgccggg tgtgctgcag    1380
accctgtttg acagtgaagg cccggtctgg ctccgggaga tgacggtcag cagcgtgtcc    1440
ggactgagcc ggttcagtga cgccgccctg cgccaggttg acggggtata cggcgcacag    1500
acggtggcgg acagcggtga gctgcgtttt aaggggggcgg taccgtcccg ctggcatacc    1560
tccctggcgg tgagcattga atatcggtaa                                      1590

<210> SEQ ID NO 5
<211> LENGTH: 70
<212> TYPE: DNA
<213> ORGANISM: Artificial Sequence
<220> FEATURE:
<223> OTHER INFORMATION: SPI-1-P1 primer

<400> SEQUENCE: 5
ttatggcgct ggaaggattt cctctggcag gcaaccttat aatttcatta gtgtaggctg    60
gagctgcttc                                                            70

<210> SEQ ID NO 6
<211> LENGTH: 70
<212> TYPE: DNA
<213> ORGANISM: Artificial Sequence
<220> FEATURE:
<223> OTHER INFORMATION: SPI-1-P2 primer

<400> SEQUENCE: 6
atgcaaaata tggtcttaat tatatcatga tgagttcagc caacggtgat catatgaata    60
tcctccttag                                                            70

<210> SEQ ID NO 7
<211> LENGTH: 21
<212> TYPE: DNA
<213> ORGANISM: Artificial Sequence
<220> FEATURE:
<223> OTHER INFORMATION: SPI-1-P3 primer

<400> SEQUENCE: 7
atgttcttaa caacgttact g                                               21

<210> SEQ ID NO 8
<211> LENGTH: 21
<212> TYPE: DNA
<213> ORGANISM: Artificial Sequence
<220> FEATURE:
<223> OTHER INFORMATION: SPI-1-P4 primer

<400> SEQUENCE: 8
aggtagtacg ttactgacca c                                               21

<210> SEQ ID NO 9
<211> LENGTH: 70
<212> TYPE: DNA
<213> ORGANISM: Artificial Sequence
<220> FEATURE:
<223> OTHER INFORMATION: SPI-2-P1 primer
```

-continued

```
<400> SEQUENCE: 9
accctcttaa ccttcgcagt ggcctgaaga agcataccaa aagcatttat gtgtaggctg    60
gagctgcttc                                                           70

<210> SEQ ID NO 10
<211> LENGTH: 70
<212> TYPE: DNA
<213> ORGANISM: Artificial Sequence
<220> FEATURE:
<223> OTHER INFORMATION: SPI-2-P2 primer

<400> SEQUENCE: 10
actgcgtggc gtaaggctca tcaaaatatg accaatgctt aataccatcg catatgaata    60
tcctccttag                                                           70

<210> SEQ ID NO 11
<211> LENGTH: 21
<212> TYPE: DNA
<213> ORGANISM: Artificial Sequence
<220> FEATURE:
<223> OTHER INFORMATION: SPI-2-P3 primer

<400> SEQUENCE: 11
tgttcgtact gccgatgtcg c                                              21

<210> SEQ ID NO 12
<211> LENGTH: 21
<212> TYPE: DNA
<213> ORGANISM: Artificial Sequence
<220> FEATURE:
<223> OTHER INFORMATION: SPI-2-P4 primer

<400> SEQUENCE: 12
agtacgacga ctgacgccaa t                                              21

<210> SEQ ID NO 13
<211> LENGTH: 70
<212> TYPE: DNA
<213> ORGANISM: Artificial Sequence
<220> FEATURE:
<223> OTHER INFORMATION: spv-P1 primer

<400> SEQUENCE: 13
gtgcaaaaac aggtcaccgc catcctgttt ttgcacatca aaacattttt gtgtaggctg    60
gagctgcttc                                                           70

<210> SEQ ID NO 14
<211> LENGTH: 70
<212> TYPE: DNA
<213> ORGANISM: Artificial Sequence
<220> FEATURE:
<223> OTHER INFORMATION: spv-P2 primer

<400> SEQUENCE: 14
ttaccccaac agcttgccgt gtttgcgctt gaacataggg atgcgggctt catatgaata    60
tcctccttag                                                           70

<210> SEQ ID NO 15
<211> LENGTH: 21
<212> TYPE: DNA
<213> ORGANISM: Artificial Sequence
<220> FEATURE:
<223> OTHER INFORMATION: spv-P3 primer
```

```
<400> SEQUENCE: 15
gaccatatct gcctgcctca g                                              21

<210> SEQ ID NO 16
<211> LENGTH: 21
<212> TYPE: DNA
<213> ORGANISM: Artificial Sequence
<220> FEATURE:
<223> OTHER INFORMATION: spv-P4 primer

<400> SEQUENCE: 16
cagagcccgt tctctaccga c                                              21

<210> SEQ ID NO 17
<211> LENGTH: 70
<212> TYPE: DNA
<213> ORGANISM: Artificial Sequence
<220> FEATURE:
<223> OTHER INFORMATION: fae-P1 primer

<400> SEQUENCE: 17
ttaccgatat tcaatgctca ccgccaggga ggtatgccag cgggacggta gtgtaggctg    60
gagctgcttc                                                           70

<210> SEQ ID NO 18
<211> LENGTH: 70
<212> TYPE: DNA
<213> ORGANISM: Artificial Sequence
<220> FEATURE:
<223> OTHER INFORMATION: fae-P2 primer

<400> SEQUENCE: 18
atgaaaataa cgcatcatta taatctatt atttccgccc tggccgcgct catatgaata     60
tcctccttag                                                           70

<210> SEQ ID NO 19
<211> LENGTH: 21
<212> TYPE: DNA
<213> ORGANISM: Artificial Sequence
<220> FEATURE:
<223> OTHER INFORMATION: fae-P3 primer

<400> SEQUENCE: 19
caggctcccc tgccaccggc t                                              21

<210> SEQ ID NO 20
<211> LENGTH: 21
<212> TYPE: DNA
<213> ORGANISM: Artificial Sequence
<220> FEATURE:
<223> OTHER INFORMATION: fae-P4 primer

<400> SEQUENCE: 20
caggccaact atctttccct a                                              21

<210> SEQ ID NO 21
<211> LENGTH: 22
<212> TYPE: DNA
<213> ORGANISM: Artificial Sequence
<220> FEATURE:
<223> OTHER INFORMATION: spv-S1 primer

<400> SEQUENCE: 21
ggtcaattaa atccactcag aa                                             22
```

```
<210> SEQ ID NO 22
<211> LENGTH: 20
<212> TYPE: DNA
<213> ORGANISM: Artificial Sequence
<220> FEATURE:
<223> OTHER INFORMATION: spv-S2 primer

<400> SEQUENCE: 22
acgggagaca ccagattatc                                              20

<210> SEQ ID NO 23
<211> LENGTH: 20
<212> TYPE: DNA
<213> ORGANISM: Artificial Sequence
<220> FEATURE:
<223> OTHER INFORMATION: spv-S3 primer

<400> SEQUENCE: 23
ttcagtaaag tggcgtgagc                                              20

<210> SEQ ID NO 24
<211> LENGTH: 20
<212> TYPE: DNA
<213> ORGANISM: Artificial Sequence
<220> FEATURE:
<223> OTHER INFORMATION: spv-S4 primer

<400> SEQUENCE: 24
ccaggtggag ttatctctgc                                              20

<210> SEQ ID NO 25
<211> LENGTH: 20
<212> TYPE: DNA
<213> ORGANISM: Artificial Sequence
<220> FEATURE:
<223> OTHER INFORMATION: spv-S5 primer

<400> SEQUENCE: 25
actgtcgggc aaaggtattc                                              20

<210> SEQ ID NO 26
<211> LENGTH: 21
<212> TYPE: DNA
<213> ORGANISM: Artificial Sequence
<220> FEATURE:
<223> OTHER INFORMATION: spv-S6 primer

<400> SEQUENCE: 26
tttctggtta ctgcatgaca g                                            21

<210> SEQ ID NO 27
<211> LENGTH: 19
<212> TYPE: DNA
<213> ORGANISM: Artificial Sequence
<220> FEATURE:
<223> OTHER INFORMATION: spv-S7 primer

<400> SEQUENCE: 27
tccagaggta cagatcggc                                               19

<210> SEQ ID NO 28
<211> LENGTH: 21
<212> TYPE: DNA
<213> ORGANISM: Artificial Sequence
<220> FEATURE:
<223> OTHER INFORMATION: spv-S8 primer
```

```
<400> SEQUENCE: 28
gaaggaatac actactatag g                                              21

<210> SEQ ID NO 29
<211> LENGTH: 20
<212> TYPE: DNA
<213> ORGANISM: Artificial Sequence
<220> FEATURE:
<223> OTHER INFORMATION: spv-S9 primer

<400> SEQUENCE: 29
gtgtcagcag ttgcatcatc                                                20

<210> SEQ ID NO 30
<211> LENGTH: 20
<212> TYPE: DNA
<213> ORGANISM: Artificial Sequence
<220> FEATURE:
<223> OTHER INFORMATION: spv-S10 primer

<400> SEQUENCE: 30
agtgaccgat atggagaagg                                                20

<210> SEQ ID NO 31
<211> LENGTH: 20
<212> TYPE: DNA
<213> ORGANISM: Artificial Sequence
<220> FEATURE:
<223> OTHER INFORMATION: spv-S11 primer

<400> SEQUENCE: 31
aagcctgtct ctgcatttcg                                                20

<210> SEQ ID NO 32
<211> LENGTH: 21
<212> TYPE: DNA
<213> ORGANISM: Artificial Sequence
<220> FEATURE:
<223> OTHER INFORMATION: spv-S12 primer

<400> SEQUENCE: 32
aaccgttatg acattaagag g                                              21

<210> SEQ ID NO 33
<211> LENGTH: 21
<212> TYPE: DNA
<213> ORGANISM: Artificial Sequence
<220> FEATURE:
<223> OTHER INFORMATION: spv-S13 primer

<400> SEQUENCE: 33
taaggctctc tattaactta c                                              21

<210> SEQ ID NO 34
<211> LENGTH: 19
<212> TYPE: DNA
<213> ORGANISM: Artificial Sequence
<220> FEATURE:
<223> OTHER INFORMATION: spv-S14 primer

<400> SEQUENCE: 34
aaccgcttct ggctgtagc                                                 19

<210> SEQ ID NO 35
<211> LENGTH: 22
<212> TYPE: DNA
```

```
<213> ORGANISM: Artificial Sequence
<220> FEATURE:
<223> OTHER INFORMATION: spv-S15 primer

<400> SEQUENCE: 35
ccgtaacaat gacattatcc tc                                              22
```